(12) United States Patent
Tatsiankou et al.

(10) Patent No.: US 10,209,132 B2
(45) Date of Patent: Feb. 19, 2019

(54) GLOBAL SOLAR SPECTRUM DEVICES AND METHODS

(71) Applicant: SPECTRAFY INC., Ottawa (CA)

(72) Inventors: Viktar Tatsiankou, Ottawa (CA); Richard Beal, Ottawa (CA)

(73) Assignee: Spectrafy Inc., Ottawa (CA)

( * ) Notice: Subject to any disclaimer, the term of this patent is extended or adjusted under 35 U.S.C. 154(b) by 0 days.

(21) Appl. No.: 15/769,601

(22) PCT Filed: Oct. 20, 2016

(86) PCT No.: PCT/CA2016/000264
§ 371 (c)(1),
(2) Date: Apr. 19, 2018

(87) PCT Pub. No.: WO2017/066865
PCT Pub. Date: Apr. 27, 2017

(65) Prior Publication Data
US 2018/0313693 A1 Nov. 1, 2018

Related U.S. Application Data

(60) Provisional application No. 62/243,706, filed on Oct. 20, 2015.

(51) Int. Cl.
*G01N 21/25* (2006.01)
*G01J 3/36* (2006.01)
(Continued)

(52) U.S. Cl.
CPC ............... *G01J 3/36* (2013.01); *G01J 1/0411* (2013.01); *G01J 1/0474* (2013.01);
(Continued)

(58) Field of Classification Search
CPC ........ G01J 3/02; G01J 3/36; G01J 1/06; G01J 1/04; G01N 21/33; H01L 31/00; H01L 31/055
See application file for complete search history.

(56) References Cited

U.S. PATENT DOCUMENTS

2009/0272424 A1* 11/2009 Ortabasi ............. H01L 31/0543
136/246

\* cited by examiner

*Primary Examiner* — Abdullahi Nur
(74) *Attorney, Agent, or Firm* — Rosenberg, Klein & Lee

(57) ABSTRACT

Solar spectral irradiance (SSI) measurements are important for solar collector/photovoltaic panel efficiency and solar energy resource assessment as well as being important for scientific meteorological/climate observations and material testing research. To date such measurements have exploited modified diffraction grating based scientific instruments which are bulky, expensive, and with low mechanical integrity for generalized deployment. A compact and cost-effective tool for accurately determining the global solar spectra as well as the global horizontal or tilted irradiances as part of on-site solar resource assessments and module performance characterization studies would be beneficial. An instrument with no moving parts for mechanical and environment stability in open field, non-controlled deployments could exploit software to resolve the global, direct and diffuse solar spectra from its measurements within the 280-4000 nm spectral range, in addition to major atmospheric processes, such as air mass, Rayleigh scattering, aerosol extinction, ozone and water vapor absorptions.

26 Claims, 20 Drawing Sheets

(51) Int. Cl.
 G01J 1/04 (2006.01)
 G01J 3/02 (2006.01)
 G01J 1/06 (2006.01)
 G01J 3/12 (2006.01)
 G01J 1/42 (2006.01)
(52) U.S. Cl.
 CPC ............... G01J 1/0492 (2013.01); G01J 1/06 (2013.01); G01J 3/0208 (2013.01); G01J 3/0262 (2013.01); G01J 2001/4266 (2013.01); G01J 2003/1213 (2013.01)

GLOBAL SOLAR SPECTRUM DEVICES AND METHODS

CROSS-REFERENCE TO RELATED APPLICATIONS

This specification claims the benefit of priority as 371 National Phase Entry application of PCT/CA2016/000,264 entitled "Global Solar Spectrum Devices and Methods" filed Oct. 20, 2016, which itself claims the benefit of priority from U.S. Provisional Patent Application 62/243,706 filed Oct. 20, 2015 entitled "Global Solar Spectrum Devices and Methods", the entire contents of each being incorporated herein by reference.

FIELD OF THE INVENTION

This invention relates to global solar spectral irradiance and more particularly to compact, no-moving part field deployable devices and methods of measuring and resolving global, direct and diffuse solar spectral irradiance, direct normal irradiance together with aerosol, water vapour and ozone spectral absorption profiles.

BACKGROUND OF THE INVENTION

Solar energy is the radiant light and heat from the Sun harnessed using a range of ever-evolving technologies such as solar heating, photovoltaics, solar thermal energy, solar architecture and artificial photosynthesis. It is an important source of renewable energy and its technologies are broadly characterized as either passive solar or active solar depending on the way they capture and distribute solar energy or convert it into solar power. Active solar techniques include the use of photovoltaic systems, concentrated solar power and solar water heating to harness the energy. Passive solar techniques include orienting a building to the Sun, selecting materials with favorable thermal mass or light dispersing properties, and designing spaces that naturally circulate air.

Photovoltaic cells, commonly referred to as solar cells, are electrical devices that convert incident light within their wavelength range of operation into electricity for immediate use or subsequent use through storage within a battery. Historically, two time-of-day dependent factors have complicated both the characterization of photovoltaic module and array performance and projected power generation in different deployment locations. These factors are the changes in the solar spectrum over the day and optical effects arising from solar angle-of-incidence. Accordingly, solar spectral irradiance (SSI) measurements are important for solar collector/photovoltaic panel efficiency and solar energy resource assessment. However, they are also important for scientific meteorological/climate observations and material testing research.

To date SSI measurements exploit modified scientific instruments based upon diffraction gratings and accordingly are generally defined by being bulky, expensive, and with low mechanical integrity for generalized deployment. Accordingly, it would be beneficial to provide a compact and cost-effective tool for accurately determining the global solar spectra as well as the global horizontal or tilted irradiances as part of on-site solar resource assessments and module performance characterization studies. It would be further beneficial for the tool to have no moving parts for mechanical and environment stability in open field, non-controlled deployments and to exploit software to resolve the global, direct and diffuse solar spectra from its measurements within the 280-4000 nm spectral range, in addition to major atmospheric processes, such as air mass, Rayleigh scattering, aerosol extinction, ozone and water vapour absorptions.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations within the prior art relating to global solar spectral irradiance and more particularly to compact, no-moving part field deployable devices and methods of measuring and resolving global, direct and diffuse solar spectral irradiance, together with aerosol, water vapour and ozone spectral absorption profiles.

In accordance with an embodiment of the invention there is provided a device comprising a spherical diffuser comprising a spherical cavity within an outer body, the spherical cavity coated with a first near Lambertian material;

a first aperture of a first predetermined diameter formed in a first predetermined position on the spherical diffuser;

a second aperture of a second predetermined diameter formed in a second predetermined position on the spherical diffuser;

a baffle disposed in a predetermined relationship relative to the first aperture and the second aperture, the baffle having a predetermined thickness, is coated with a second near Lambertian material and is disposed on the inner surface of the spherical diffuser and having a geometry defining a predetermined portion of a sphere;

a plurality of optical collimators coupled to the second aperture and defining a maximum angular acceptance angle for each photodetector of a plurality of photodetectors disposed at the distal end of an optical collimator from that coupled to the second aperture; and a plurality of optical filters, each filter having a passband of predetermined optical wavelengths and disposed in combination with an optical collimator of the plurality of collimators to filter optical signals exiting the second aperture.

In accordance with an embodiment of the invention there is provided a device comprising a plurality of first photodetectors, each first photodetector receiving a predetermined wavelength range of the ambient optical environment via an optical path comprising a diffuser element, a bandpass filter, and an optical collimator to limit the angle of incident ambient light within a predetermined field of view;

a plurality of second photodetectors arranged radially around a post projecting above the upper surface of the plurality of second photodetectors; and an electronic circuit comprising a first portion for digitizing a photocurrent for each first photodetector of the plurality of first photodetectors, a second portion for digitizing a photocurrent for each second photodetector of the plurality of second photodetectors, and a third portion for generating a reconstructed solar spectrum in dependence upon at least the digitized photocurrents of the plurality of first photodetectors, the digitized photocurrents of the plurality of second photodetectors, and a model of the solar spectrum with no atmosphere.

In accordance with an embodiment of the invention there is provided a device comprising:

a plurality of wavelength filtered photodetectors each receiving light from the ambient environment within a predetermined wavelength range and within a predetermined angle of incidence to the normal of the photodetector;

a plurality of second photodetectors each receiving light from the ambient environment;

a shadow pole disposed with respect to the plurality of second photodetectors; and an optical element disposed on a front face of the device comprising:

a first uniform transparent region disposed in front of the plurality of second photodetectors and a second diffuser region comprising a plurality of features, each feature designed in dependence upon a predetermined wavelength associated with a wavelength filtered photodetector and the material from which the optical element is formed.

a transparent dome that sits above the front surface of the device and protects the diffuser, shadow pole and second plurality of photodiodes from the elements.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
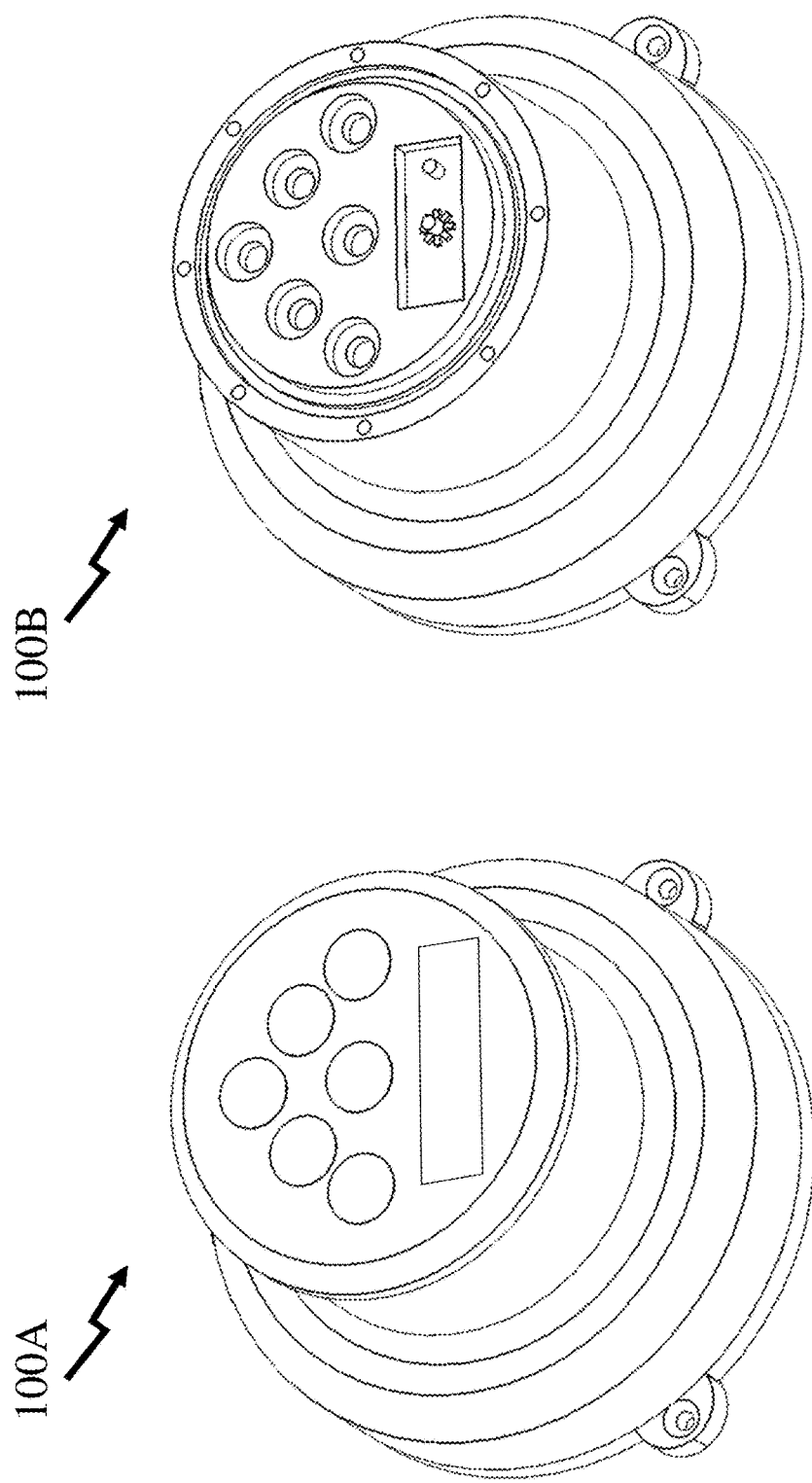
FIG. 1 depicts a global solar spectral irradiance meter (SolarSIM-G) according to an embodiment of the invention with diffuser attached and removed.

The present invention is directed to global solar spectral irradiance and more particularly to compact, no-moving part field deployable devices and methods of measuring and resolving global, direct and diffuse solar spectral irradiance, together with aerosol, water vapour and ozone spectral absorption profiles.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users. Reference to terms "including", "comprising", "consisting" and grammatical variants thereof do not preclude the addition of one or more components, features, steps, integers or groups thereof and that the terms are not to be construed as specifying components, features, steps or integers. Likewise, the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, a wearable device and an electronic reader.

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, a gaming console, a digital set-top box, an analog set-top box, an Internet enabled appliance, an Internet enabled television, and a multimedia player.

A "server" as used herein, and throughout this disclosure, refers to one or more physical computers co-located and/or geographically distributed running one or more services as a host to users of other computers, PEDs, FEDs, etc. to serve the client needs of these other users. This includes, but is not limited to, a database server, file server, mail server, print server, web server, gaming server, or virtual environment server.

An "application" (commonly referred to as an "app") as used herein may refer to, but is not limited to, a "software application", an element of a "software suite", a computer program designed to allow an individual to perform an activity, a computer program designed to allow an electronic device to perform an activity, and a computer program designed to communicate with local and/or remote electronic devices. An application thus differs from an operating system (which runs a computer), a utility (which performs maintenance or general-purpose chores), and programming tool (with which computer programs are created). Generally, within the following description with respect to embodiments of the invention an application is generally presented in respect of software permanently and/or temporarily installed upon a PED and/or FED.

"Electronic content" (also referred to as "content" or "digital content") as used herein may refer to, but is not limited to, any type of content that exists in the form of digital data as stored, transmitted, received and/or converted wherein one or more of these steps may be analog although generally these steps will be digital. Forms of digital content include, but are not limited to, information that is digitally broadcast, streamed or contained in discrete files. Viewed narrowly, types of digital content include popular media types such as MP3, JPG, AVI, TIFF, AAC, TXT, RTF, HTML, XHTML, PDF, XLS, SVG, WMA, MP4, FLV, and PPT, for example, as well as others, see for example http://en.wikipedia.org/wiki/List_of_file_formats. Within a broader approach digital content mat include any type of digital information, e.g. digitally updated weather forecast, a GPS map, an eBook, a photograph, a video, a Vine™, a blog posting, a Facebook™ posting, a Twitter™ tweet, online TV, etc. The digital content may be any digital data that is at least one of generated, selected, created, modified, and transmitted in response to a user request, said request may be a query, a search, a trigger, an alarm, and a message for example.

A "scaffold" or "scaffolds" as used herein, and throughout this disclosure, refers to a structure that is used to hold up, interface with, or support another material or element(s). This includes, but is not limited to, such two-dimensional (2D) structures such as substrates and films, three-dimensional (3D) structures such as geometrical objects, non-geometrical objects, combinations of geometrical and non-geometrical objects, naturally occurring structural configurations, and manmade structural configurations. A scaffold may be solid, hollow, and porous or a combination thereof. A scaffold may contain recesses, pores, openings, holes, vias, and channels or a combination thereof. A scaffold may be smooth, textured, have predetermined surface profiles and/or features. A scaffold may be intended to support one or more other materials, one or more films, a multilayer film, one type of particle, multiple types of particles etc. A scaffold may include, but not be limited to, a spine of a device and/or a framework, for example, which also supports a shell and/or a casing.

A "shell" as used herein, and throughout this disclosure, refers to a structure that is used to contain and/or surround at least partially and/or fully a number of elements within a device according to embodiments of the invention. A shell may include, but not limited to, a part or parts that are mounted to a scaffold or scaffolds that support elements within a device according to an embodiment of the invention.

A "casing" as used herein, and throughout this disclosure, refers to a structure surrounding a scaffold and/or shell. This includes structures typically formed from an elastomer and/or silicone to provide a desired combination of properties to the device it forms part of and other properties including, but not limited to, hermeticity, liquid ingress barrier, solid particulate ingress barrier, surface sheen, physical tactile surface, and colour. A casing may include, but not limited to, a part or parts that are mounted to a scaffold or scaffolds and/or a casing or casings forming part of a device according to an embodiment of the invention.

A "polyester" as used herein, and throughout this disclosure, refers to a category of polymers that contain the ester functional group in their main chain. This includes, but is not limited to polyesters which are naturally occurring chemicals as well as synthetics through step-growth polymerization, for example. Polyesters may be biodegradable or not. Polyesters may be a thermoplastic or thermoset or resins cured by hardeners. Polyesters may be aliphatic, semi-aromatic or aromatic. Polyesters may include, but not be limited to, those exploiting polyglycolide, polylactic acid (PLA), polycaprolactone (PCL), polyhydroxyalkanoate (PHA), polyhydroxybutyrate (PHB), polyethylene adipate (PEA), polybutylene succinate (PBS), polyethylene terephthalate (PET), polybutylene terephthalate (PBT), polytrimethylene terephthalate (PTT), and polyethylene naphthalate (PEN).

A "thermoplastic" or "thermosoftening plastic" as used herein and throughout this disclosure, refers to a category of polymers that become pliable or moldable above a specific temperature and solidify upon cooling. Thermoplastics may include, but not be limited, polycarbonate (PC), polyether sulfone (PES), polyether ether ketone (PEEK), polyethylene (PE), polypropylene (PP), poly vinyl chloride (PVC), polytetrafluoroethylene (PTFE), polyimide (PI), polyphenylsulfone (PPSU), polychlorotrifluoroethene (PCTFE or PTFCE), florinated ethylene propylene (FEP), and perfluoroalkoxy alkane (PFA).

A "metal" as used herein, and throughout this disclosure, refers to a material that has good electrical and thermal conductivity. Such materials may be malleable and/or fusible and/or ductile. Metals may include, but not be limited to, aluminum, nickel, copper, cobalt, chromium, silver, gold, platinum, iron, zinc, titanium, and alloys thereof such as bronze, stainless steel, brass, and phosphor bronze.

A "silicone" as used herein, and throughout this disclosure, refers to a polymer that includes any inert, synthetic compound made up of repeating units of siloxane.

An "elastomeric" material or "elastomer" as used herein, and throughout this disclosure, refers to a material, generally a polymer, with viscoelasticity. Elastomers may include, but not be limited to, unsaturated rubbers such as polyisoprene, butyl rubber, ethylene propylene rubber, silicone rubber, fluorosilicone rubber, fluoroelastomers, perfluoroelastomers, and thermoplastic elastomers.

A global spectral irradiance meter (SolarSIM-G) is an instrument for resolving the global, direct and diffuse solar spectral irradiance together with aerosol, water vapour and ozone spectral absorption profiles over a predetermined wavelength range, for example 280 nm≤λ≤4000 nm as described below with respect to the embodiment of the invention depicted in FIGS. 1 to 10. Accordingly, the SolarSIM-G according to embodiments of the invention combines capabilities from multiple instruments such as a spectroradiometer, pyranometer, sun photometer, pyheliometer and a weather station all in one single compact housing. As described below in respect of an embodiment of the invention in FIGS. 1 to 10 the SolarSIM-G provides six spectral channels although it would be evident that more or less spectral channels can be implanted although, typically, reductions will result in corresponding performance and/or feature reduction. Accordingly, a SolarSIM-G according to an embodiment of the invention comprises:

a plurality of spectral channels in conjunction with custom shaped mini-diffusers for each spectral channel to optimize its cosine response;
a diffuse light sensor;
other ambient environmental sensors as measure inputs; and
software algorithm that resolves the global, direct, and diffuse solar spectra, along with spectral, atmospheric aerosol, water vapour and ozone transmission profiles.

As will become evident from the description below in respect of FIGS. 1 to 9 each spectral channel comprises a photodiode-collimation tube-band pass filter combination which limits the field of view that each photodiode senses from the filter. This eliminates high incident angle light from hitting the photodiodes which eliminates the central wavelength shift that the band-pass filters exhibit with high incident angle light.

As will become evident from the description below in respect of FIGS. 1 to 9 the diffuse irradiance sensor consists of a shadow pole surrounded by several small photodiodes that enable the device to estimate the ratio of diffuse/global light and estimate the diffuse irradiance. The knowledge of diffuse to global ratio allows the SolarSIM-G to actively correct for the cosine response of the instrument and aids the software algorithm in resolving the global, direct and diffuse solar spectra.

Figure 2:
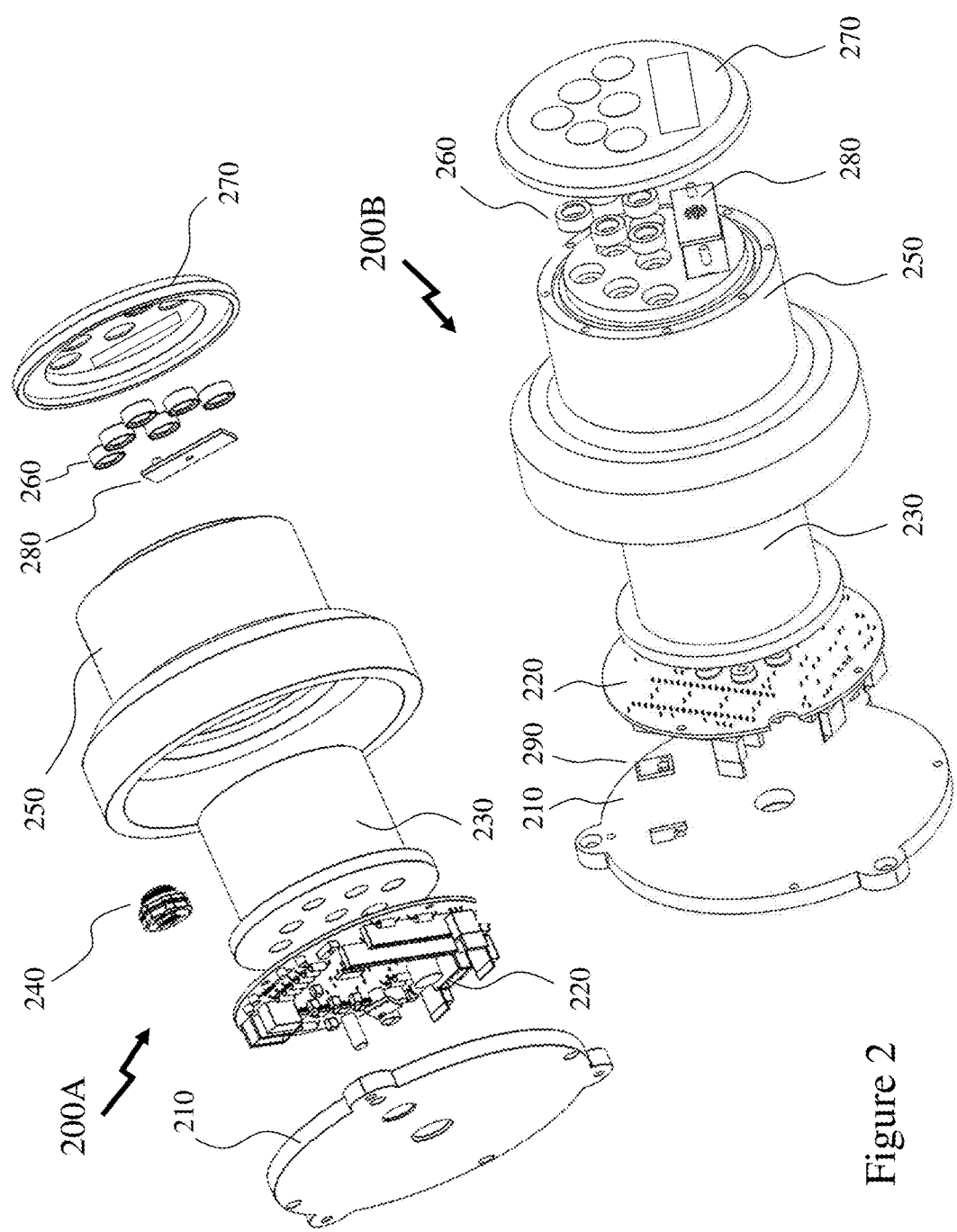
FIG. 2 depicts exploded assembly views of the SolarSIM-G according to an embodiment of the invention depicted in FIG. 1.

Referring to FIG. 1 there are depicted first and second three-dimensional (3D) perspective views 100A and 100B respectively of a SolarSIM-G according to an embodiment of the invention with and without the front diffuser plate attached. In FIG. 2 first and second 3D perspective views 200A and 200B respectively are depicted of the SolarSIM-G as an exploded assembly. The SolarSIM-G depicted in FIGS. 1 to 3 being a 6 channel design operating over a predetermined wavelength range, e.g. 280 nm≤λ≤4000 nm. Accordingly, the descriptions in respect of FIGS. 2-9 reflect this 6 channel design but it would be evident to one of skill in the art that alternate embodiments with varying channel counts may be implemented. Similarly, it would be evident that elements such as the diffuse light sensor may be omitted. As depicted the elements include Diffuser plate 270;
Optical bandpass interference filters 260;
Diffuse Light and Temperature Sensor (DILITS) 280;
Enclosure 250
Collimation tube 230;
Main PCB 220;
Ambient environment sensor 290;
Backplate 210, and
Waterproof membrane vent 240.

Figure 4:
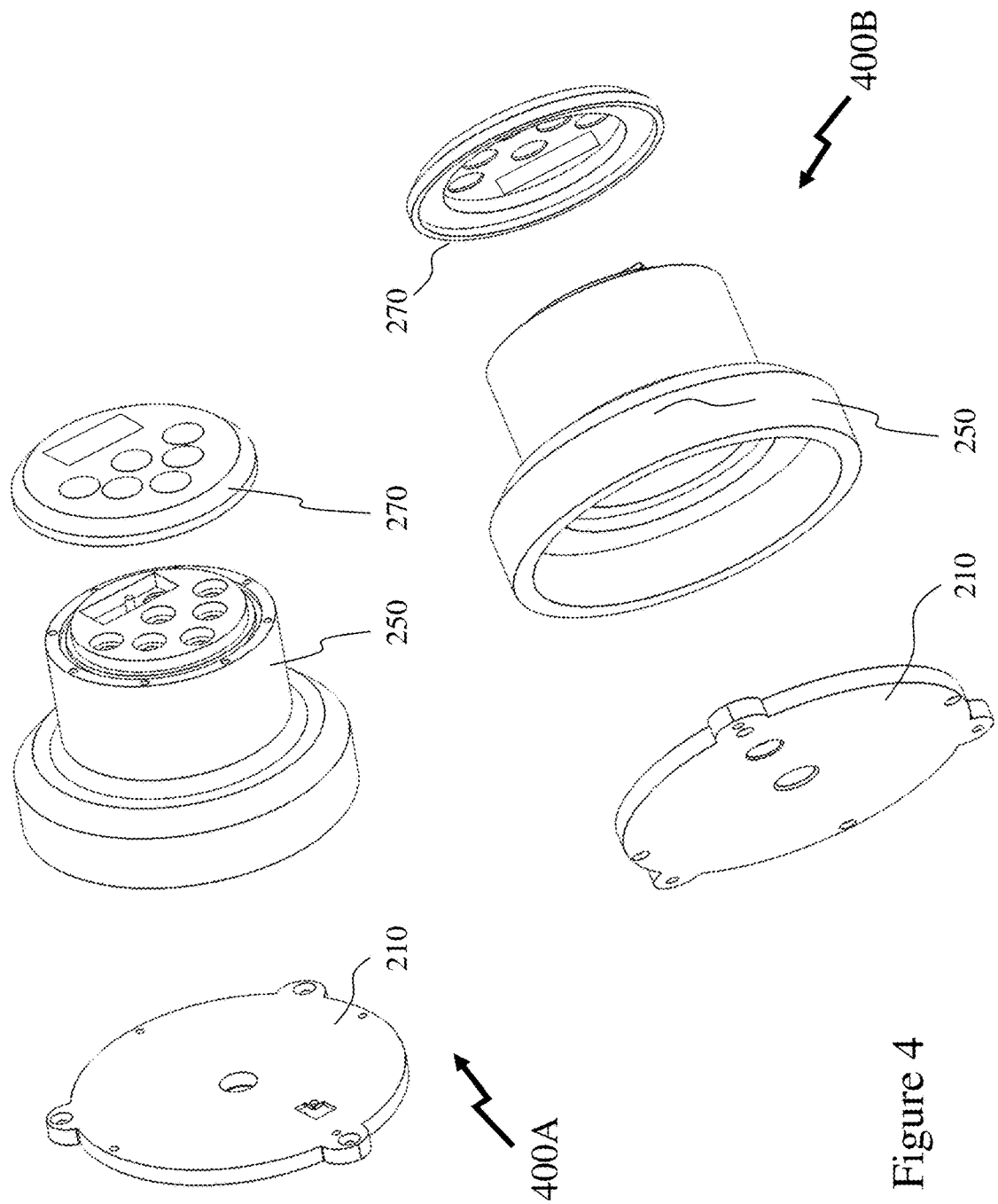
FIG. 4 depicts exploded views of the SolarSIM-G housing according to an embodiment of the invention depicted in FIG. 1.
Figure 5:
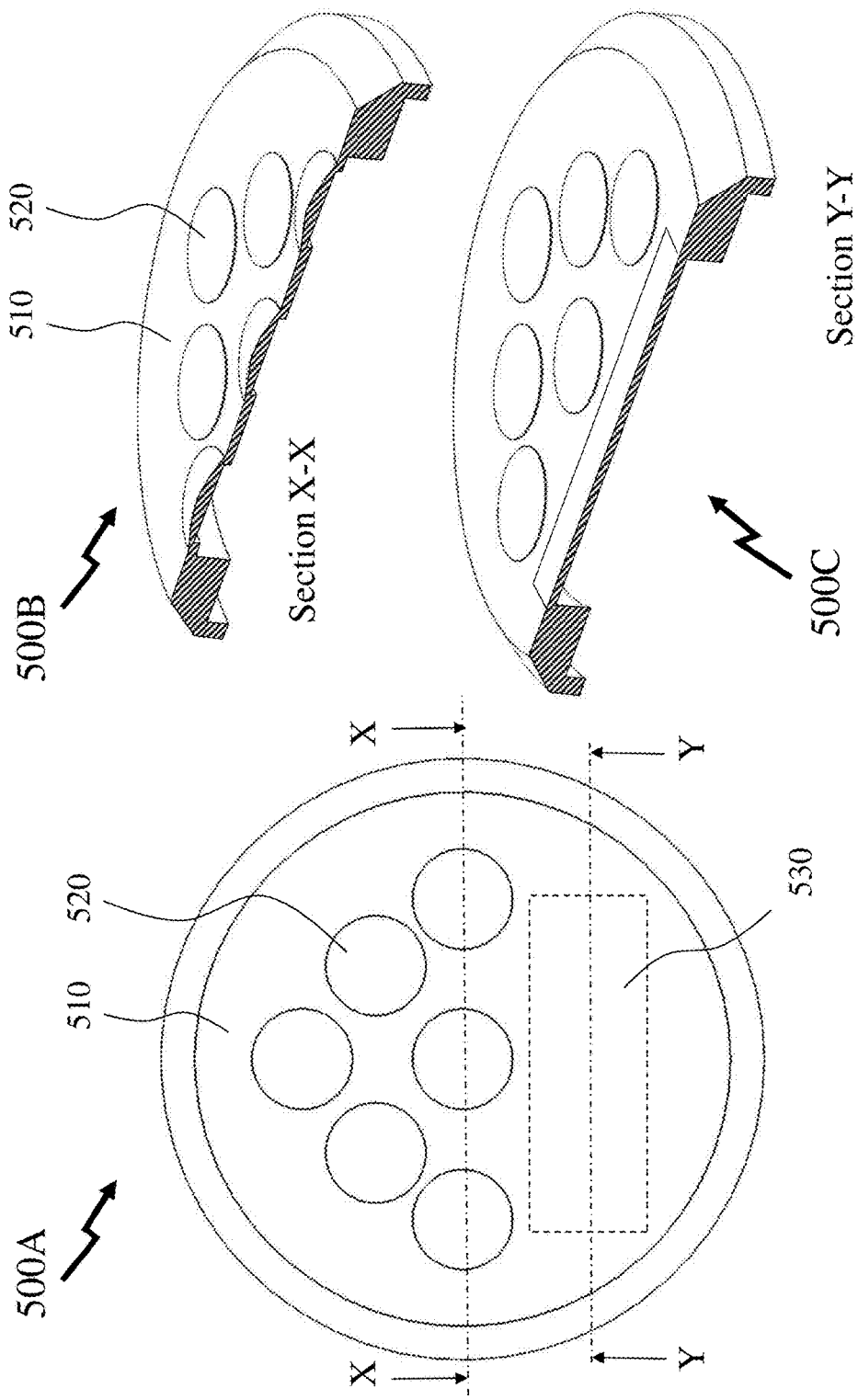
FIG. 5 depicts a plan view and cross-sectional perspective views of a diffuser plate according to an embodiment of the invention as employed within the SolarSIM-G according to an embodiment of the invention depicted in FIG. 1.

Now referring to FIG. 4 there are depicted first and second 3D perspective views 400A and 400B respectively of the SolarSIM-G external housing elements which provide the exterior surfaces of the SolarSIM-G and the barriers to direct ingress etc. both directly and at their interfaces. These external housing elements comprising baseplate 210, enclosure 250, and diffuser plate 270. As depicted the enclosure 250 forms the majority of the external housing to which the diffuser plate 270 mounts on the top and the baseplate 210 to the bottom.

The diffuser plate 270 receives the light from an entire hemisphere and scatters it an all directions (forward and backward). For the optical wavelength range of 280 nm≤λ≤4000 nm, for this embodiment of the invention, PTFE or Teflon™ are examples of materials for forming the diffuser. The diffuser plate 270 scatters the light incident on the upper face of the SolarSIM-G and is required to scatter independently of incident angle such that the light to a photodetector is coupled at all incident angles in order to achieve a good cosine response. Without a diffuser plate 270, at large incident angles the light would be mostly reflected and would not be detected, and a cosine response is not achieved. The SolarSIM-G diffuser plate 270, as pictured in FIG. 5 in first to third views 500A to 550C provides a dual functionality. It acts as a front cover for the shadow pole and photodetectors and a diffuser for the wavelength selective photodetectors at the same time. The six protruding areas 520 of the diffuser body 510 are diffusers for each wavelength filter within the SolarSIM-G. The geometry of these six mini-diffusers is optimized to achieve the best cosine response for its corresponding wavelength range of interest. Each filter therefore has a specific diffuser 520 design in the embodiment depicted. However, in other embodiments of the invention depending upon the design of the diffuser and the optical properties of the different diffuser designs may be required or in some embodiments may not be required for one, two or more of the wavelength channels. The window 530 within the diffuser plate 270 is transparent and provides a cover to the shadow pole and its associated photodetectors.

Within embodiments of the invention the diffuser plate 270 may be formed from an optically transparent material over the wavelength range of interest and the protruding areas 520 are made diffusing through processing of the material, e.g. sandblasting, etching etc. leaving the window 530 transparent. Alternatively, the body of the diffuser element may be formed from a diffusing but optically transparent material over the wavelength range of interest and the window 530 is formed from a separate material which is clear and optically transparent material over the wavelength range of interest.

Within other embodiments of the invention the SolarSIM-G diffuser plate 270 may be formed from other materials transparent over the wavelength range of interest such as a glass for example. Optionally, the SolarSIM-G diffuser plate 270 may be formed from two or more elements rather than a single piece or even different diffuser elements per channel. In other embodiments the diffuser may be transparent and may be frosted and/or translucent.

As depicted in FIGS. 1 to 9 the SolarSIM-G employs six channels with center wavelengths (CWLs) at approximately 410-430 nm, 480-505 nm, 600-620 nm, 670-690 nm, 860-880 nm, and 930-960 nm. Further, the region of the diffuser body 510 above the DILITS 280, depicted as area 530, may be flat, as depicted, or alternatively employ a surface profile. As evident in second view 500B with cross-section X-X the inner surface of the diffuser body 510 there is a recess to align each filter with its respective mini-diffuser. Further, as evident in third view 500C with cross-section Y-Y the region of the diffuser body 510 above the DILITS 280 is also recessed.

Figure 6:
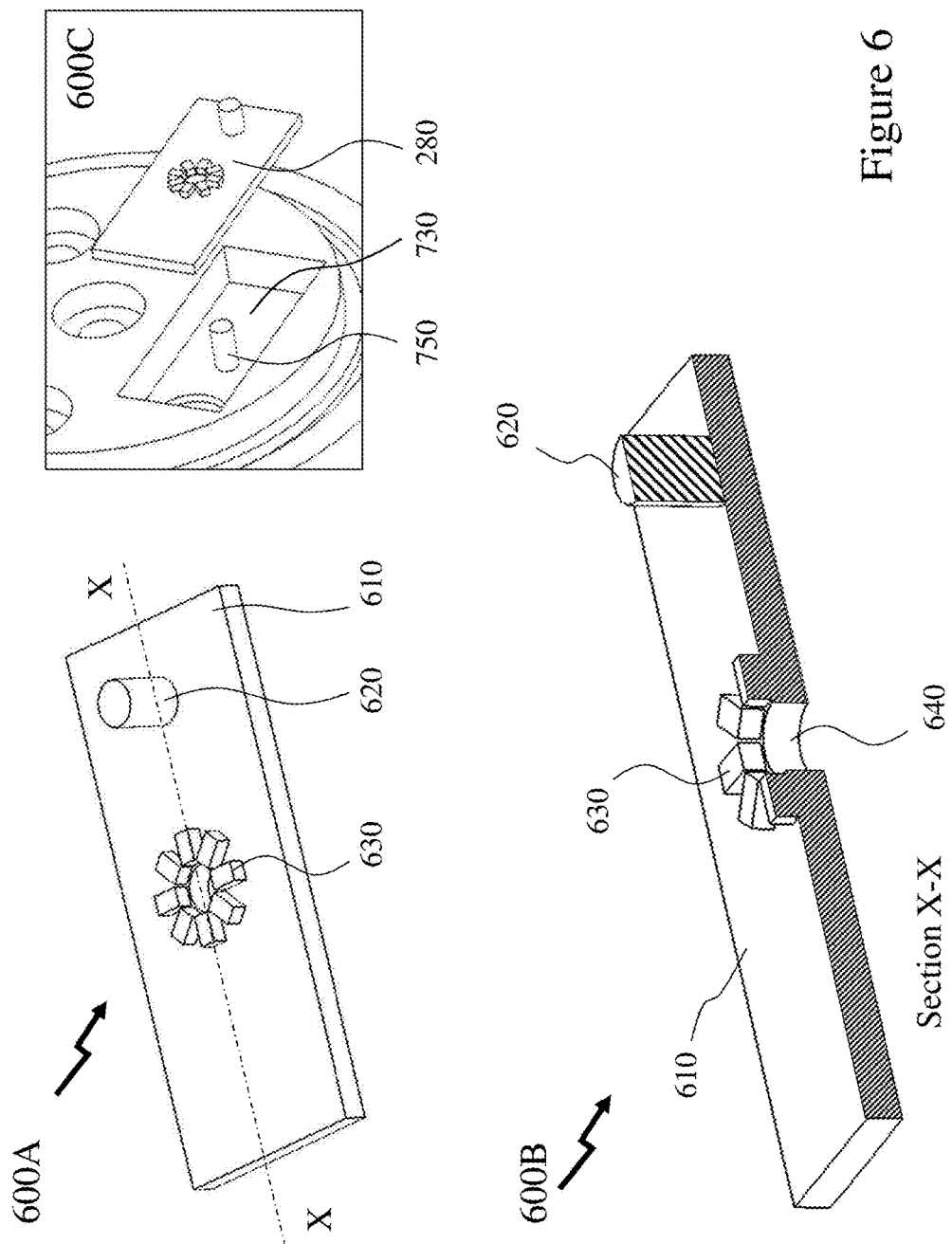
FIG. 6 depicts a perspective view and cross-sectional perspective views of a shadow pole and photodetector element according to an embodiment of the invention as employed within the SolarSIM-G according to an embodiment of the invention depicted in FIG. 1.
Figure 7:
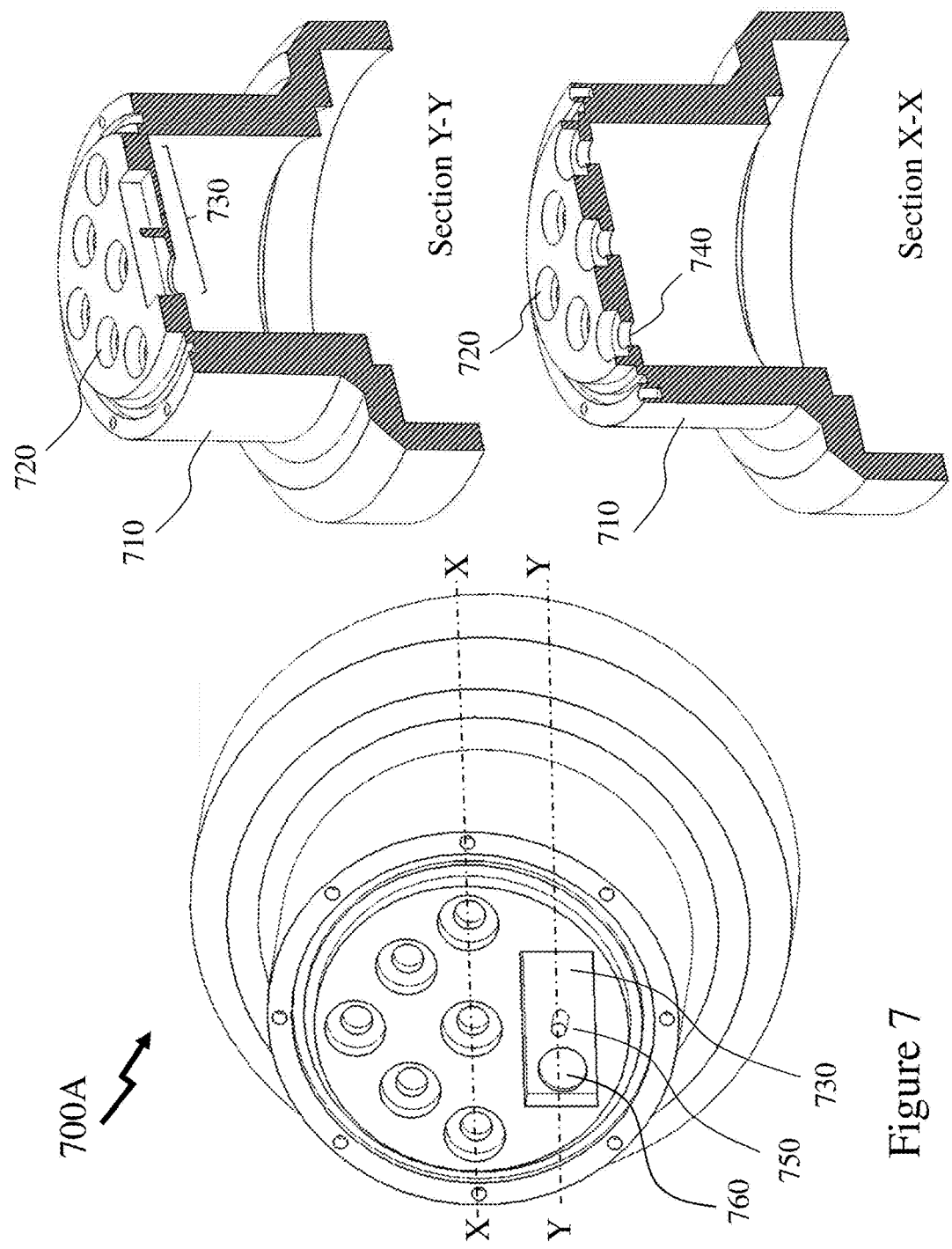
FIG. 7 depicts a perspective view and cross-sectional perspective views of a filter and enclosure according to an embodiment of the invention as employed within the SolarSIM-G according to an embodiment of the invention depicted in FIG. 1.

The DILITS 280 within the SolarSIm-Gas depicted in FIGS. 1 to 4 allows the G-SolarSIM to determine the ratio of the global incident irradiance versus the diffuse irradiance. As depicted in FIG. 6 with 3D perspective view 600A and cross-sectional 3D perspective view 600B this is accomplished through the use of a shadow pole 750 (protruding metallic piece) formed within the upper surface of the external enclosure together with a recess 730 into which the DILITS 280 sits. The shadow pole 750 projects through an opening 640 within the DILITS 280 and is surrounded by several small photodetectors 630 which are mounted to a PCB 610 which forms the bulk of the DILITS 280. Optionally, the small photodetectors 630 may be replaced by one or more detector arrays. Throughout the day, the sun's apparent motion in the sky causes the shadow pole 750 to cast its shadow onto different photodiodes 630. This blocks the direct beam of sunlight from those photodiodes 630 that are shadowed, and we can effectively estimate the diffuse irradiance in relative terms. Optionally, the region of the diffuser body 510 over the DILITS 280 may be transparent rather than diffusing or translucent. The photodetectors 630 that are not covered by the shadow report the global irradiance (diffuse+direct beam irradiance) whilst those that are covered report the diffuse beam irradiance. The ratio of the two provides information about the magnitude of the diffuse irradiance and the atmospheric conditions. For example, on a very cloudy day, we can expect the readings from each photodetector to be approximately the same. On a clear day, the shadowed photodetectors will report low irradiance, whilst the others will report relatively high irradiance.

The knowledge of the diffuse to direct beam ratio is important for several reasons. The active cosine response correction can be performed on the instrument if this ratio is known. Under laboratory conditions, the instruments cosine response is determined by having a nearly collimated light source shine light onto the instrument at various angles. The response of the instrument is compared against an ideal cosine response and a correction is obtained. However, under outdoor conditions, the instrument does not "know" how much light is coming directly at some angles versus the other angles. By establishing the direct to diffuse ratio we can accurately determine how much light is coming from the direct beam irradiance as we know the position of the sun at all times throughout the day.

The shadow pole is positioned "behind" the filters to eliminate the shadowing of the filters at low solar elevations angles. Within an embodiment of the invention, the shadow pole is oriented due north, while the arrow like arrangement of the filters points to the south. The DILITS 280 also includes a temperature sensor 620 for adjusting the transmission of the diffuser for temperature. It is conveniently positioned on the diffuse light sensor PCB 610, which is connected to the main PCB 220.

The enclosure 250 provides the means to hold everything together and protects components from the weather elements. The enclosure 250 as depicted in FIGS. 1 to 4 is depicted in 3D perspective view 700A and first and second cross-section 3D perspective views 700B and 700C respectively in FIG. 7. As depicted the upper outer surface comprises the recess 730 within which is shadow pole 750 as well as opening 760. Also depicted are the six filter recesses 720 within each of which is an aperture 740. The upper surface also contains an O-ring slot for the insertion/placement of an O-ring between the enclosure and the diffuser which allows the diffuser to seal the enclosure against moisture and debris ingress. The enclosure also has a cavity for desiccant to regulate the humidity inside the device.

Each of the bandpass interference filters pass a narrow band of light to the photodiode around their CWL. For the embodiment described in respect of FIGS. 1 to 9 these CWLs are at approximately 410-430 nm, 480-505 nm, 600-620 nm, 670-690 nm, 860-880 nm, and 930-960 nm respectively. These can be off-the-shelf hard-coated and rugged filters capable of withstanding outdoor environments. Within the embodiment of the invention described with respect to FIGS. 1 to 9 the filters are circular and may be discrete or within a housing wherein the geometry and depth of the recesses on the enclosure and diffuser adapt to suit.

Figure 3:
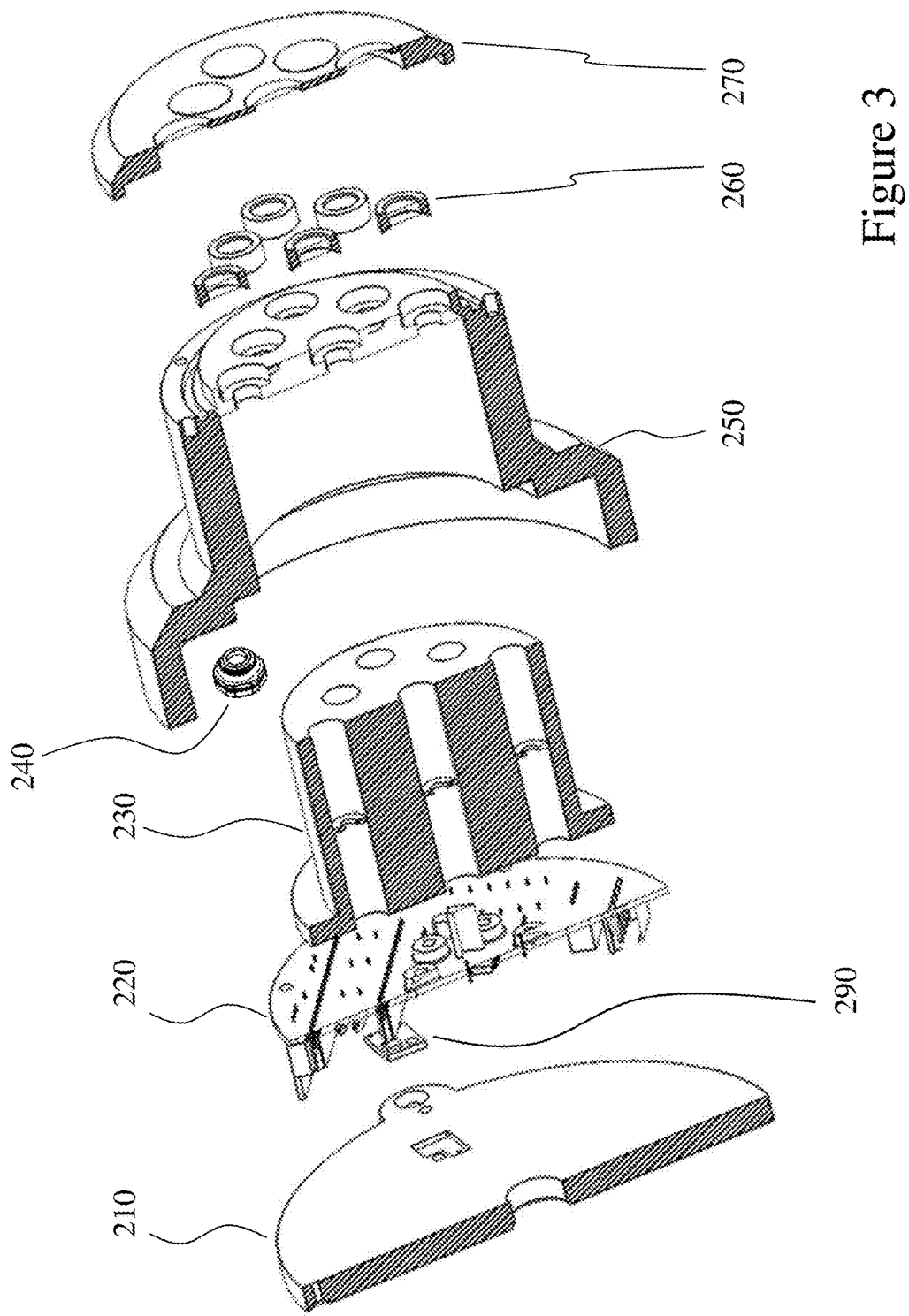
FIG. 3 depicts an exploded cross-sectional assembly view of the SolarSIM-G according to an embodiment of the invention depicted in FIG. 1.

Within the enclosure as depicted in FIGS. 2 to 3 sits a collimation tube 230 as depicted by 3D perspective view 800A, end-view 800B, and first and second cross-sections 800C and 800D representing cross-sections X-X and Y-Y respectively. The function of the collimation tube 230 is to limit the photodiodes view to light within a specific range of angular incidence. The bandpass interference filters are designed to operate at normal incidence. The center wavelength blue-shifts (approaches UV spectral range) as the incidence angle increases. However, most bandpass interference filters exhibit negligible shift up at angles of incidence of 0°-10°. Therefore, the purpose of the collimation tube is to "filter out" the light for angles greater than near optimal angle of acceptance (which depends on the filter specifications).

The collimation tube 230 is coated to minimize absorption across the wavelengths of interest, namely 280 nm≤λ≤4000 nm. For example, an aluminium baffle with black anodizing provides one physical embodiment. Each collimation tube comprises a tube within which are baffles in order to prevent light reflecting off the walls and onto the detectors. The walls may also be threaded or have their surfaces modified to minimize specular reflections. Since the collimation tube 230 is a separate component to the enclosure, the latter doesn't have to be black anodized or treated in the same manner to absorb light.

Figure 8A:
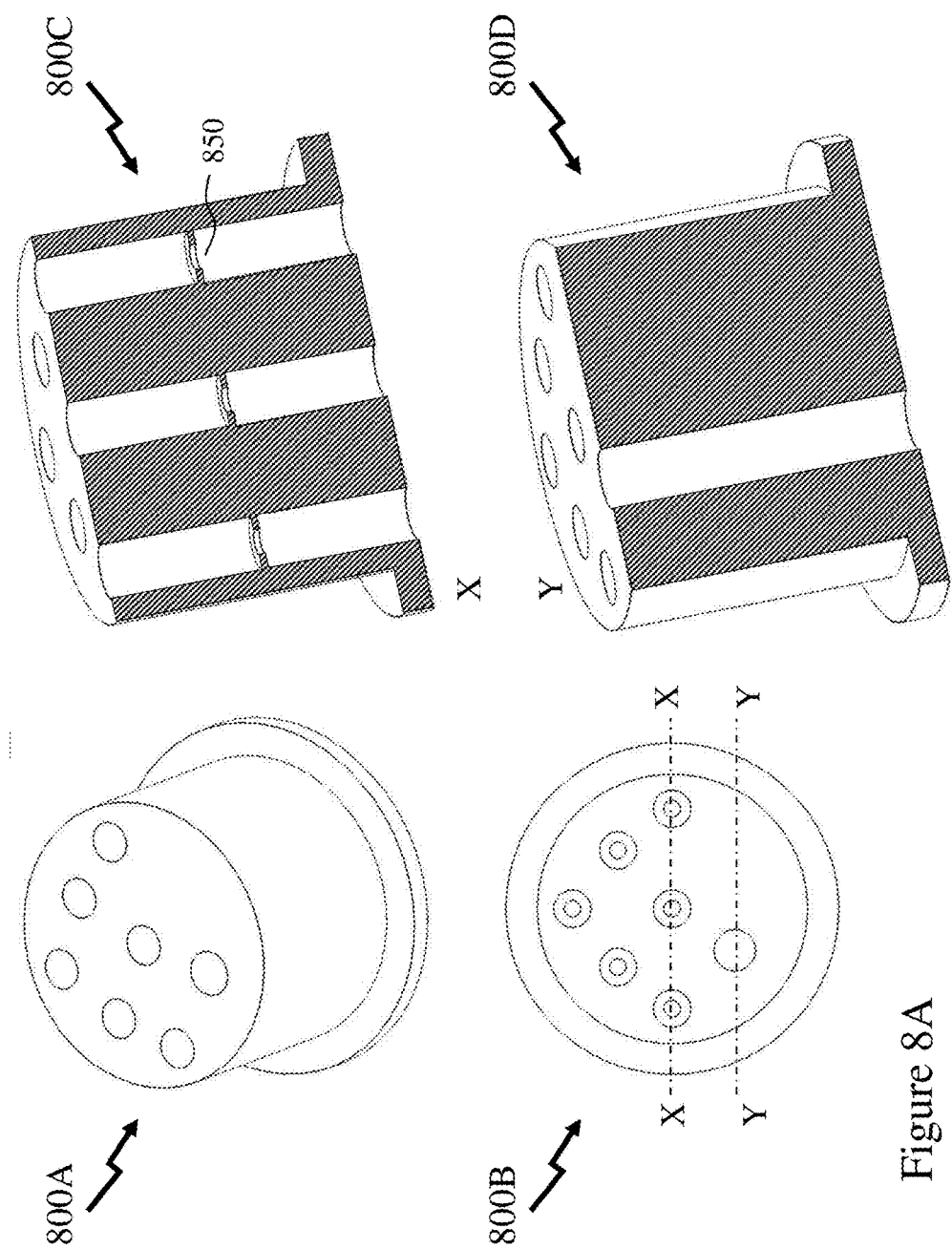
FIG. 8A depicts a perspective view and cross-sectional perspective views of a tube collimator according to an embodiment of the invention as employed within the SolarSIM-G according to an embodiment of the invention depicted in FIG. 1.
Figure 8B:
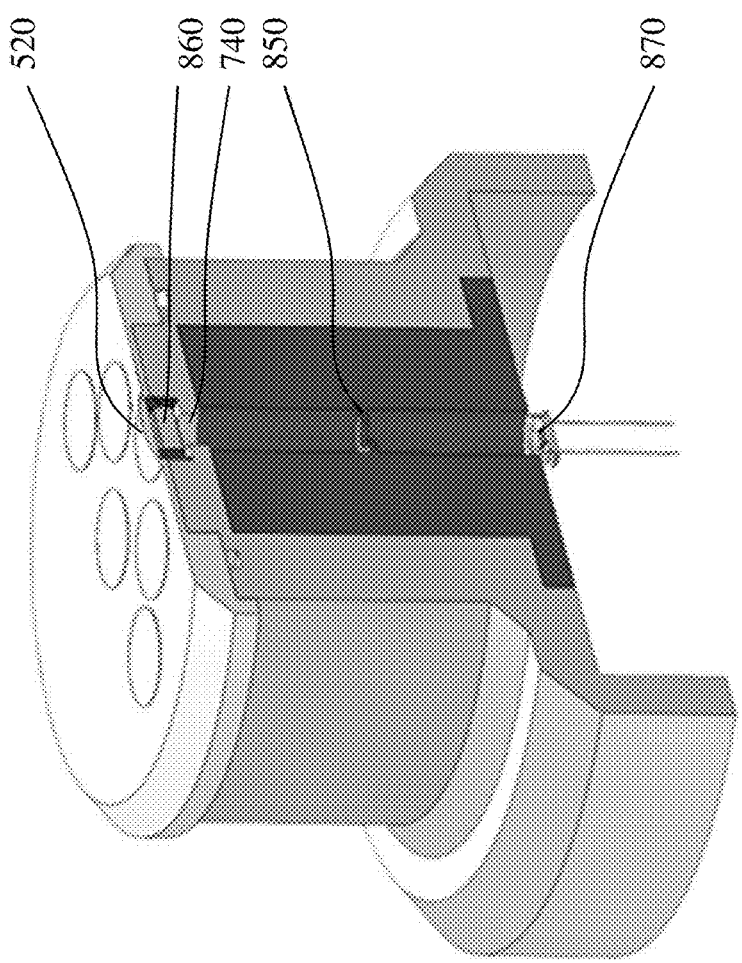
FIG. 8B depicts the optical path within an embodiment of the invention as employed within the SolarSIM-G according to an embodiment of the invention depicted in FIG. 1.

The optical path is shown in FIG. 8B where the incoming light undergoes the following transformation:
the diffuser 520 scatters the light in all directions
the scattered light passes through the filter 860
the filtered scattered light is limited by the front aperture 740;
the remaining light that has the right incidence angle passes through the baffle 850 and hits the active area of the associated photodiode 870.

The photodetectors 870 are electrically coupled to a main PCB 220 which is positioned at the bottom of the collimation tube 230 and retained together with the collimation tube 230 by the enclosure 250 and back plate 210. The enclosure 250 and back plate may be similarly designed with an O-ring seal and screw/bolt mounting as the diffuser plate 270 is attached to the enclosure 250 although other liquid and particle barriers may be employed within other embodiments of the invention such as soldering the back plate 210 onto the enclosure 250 or employing a gasket between the enclosure 250 and the back plate 210. The main PCB 220 provides all of the analog data acquisition and passes this information through a communications protocol to a host. For example, an RS-485 communication protocol may be employed from the SolarSIM-G to a host computer. However, it would be evident that the SolarSIM-G and host computer may be linked by other wired and wireless protocols including but not limited to IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-1000, DSL, Dial-Up, DOCSIS, Ethernet, G.hn, ISDN, MoCA, PON, and Power line communication (PLC). Optionally, the host computer may be associated with an installation, for example, of which the SolarSIM-G forms part. In other embodiments of the invention the host may be remote and, in some instances, may be a remote server rather than a remote computer.

Also connected to the main PCB 220 are the diffuse light sensor PCB 610 and ambient environment PCB 290, the latter of which senses ambient temperature, pressure and humidity. The later, in order to accomplish the desired measurement is connected to a waterproof membrane vent 240 that allows ambient air to pass through but not water. The ambient PCB 220 monitoring the environment is sealed with silicone or O-ring to the waterproof membrane vent 240 which may also provide for pressure equalization between the inner environment of the SolarSIM-G and ambient external environment.

Within embodiments of the invention an outer protective cover, e.g. dome, may be deployed to protect the diffuser element from the ambient environment. This outer protective cover being designed such that it allows the sunlight to impinge upon the shadow pole and the plurality of detectors around the shadow pole in addition to the collimator tubes for the wavelength filtered channels. Within embodiments of the invention with a dome it would be evident that the diffuser element may be designed according to different design guidelines as the diffuser element is now not providing environmental protection. Accordingly, the window (e.g. window 530 in FIG. 5) may be omitted such that no other element is disposed between the shadow pole and the dome. In this instance the diffuser element (e.g. diffuser element 510) may be disposed to only cover part of the upper surface of the SolarSIM-G. Optionally, the diffuser structures, e.g. protruding areas 520, may be disposed only within the collimator tube openings or within and around the collimator tubes.

Optionally, a fan may be disposed to blow periodically and/or continuously across the outside of the outer protective cover in order to mitigate soiling.

Figure 9:
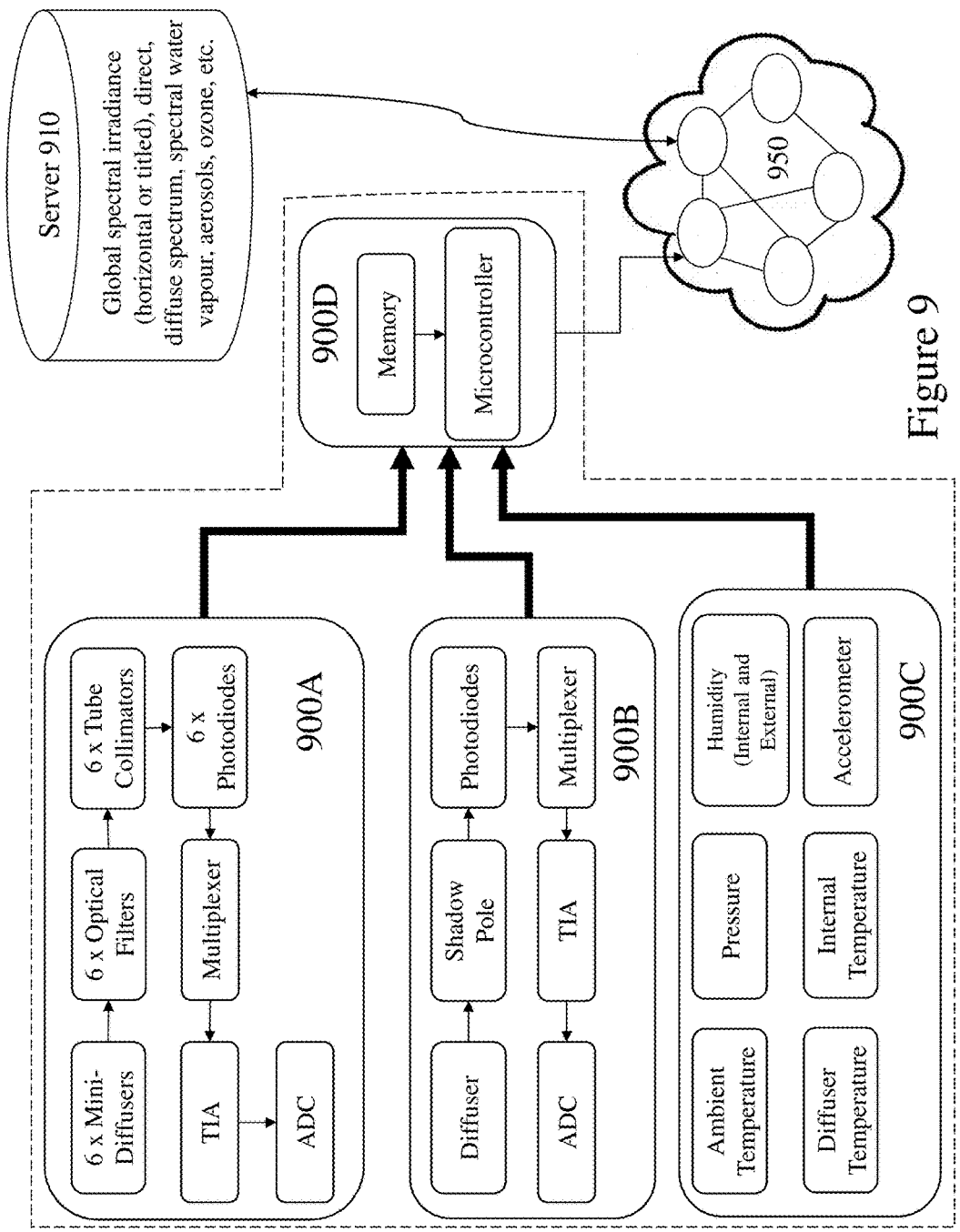
FIG. 9 depicts an assembly structure and data flow for a SolarSIM-G according to an embodiment of the invention depicted in FIG. 1.

Now referring to FIG. 9 there is depicted an exemplary system block diagram of a SolarSIM-G according to an embodiment of the invention as depicted in FIGS. 1 to 8 respectively comprising first to fourth functional blocks 900A to 900D respectively. As depicted first functional block 900A relates to the multiple wavelength channels and consists for each wavelength a mini-diffuser, optical filter, optical collimator (tube) collimator, photodiode and multiplexer. The output of the multiplexer is coupled to a transimpedance amplifier (TIA) and converted to digital form via an analog-to-digital converter (ADC). The output of the ADC is coupled to the electronic functional block 900D. Within another embodiment of the invention each photodetector has an associated TIA and the multiple TIA outputs are multiplexed for the ADC or multiple ADCs.

Second functional block 900B relates to diffuse/direct irradiance and comprises the diffuser, shadow pole, photodetectors around the shadow pole, wherein the photodetector outputs are multiplexed and coupled to the TIA and converted to digital form via an analog-to-digital converter (ADC). Optionally, the photodetector outputs are coupled to TIAs and then multiplexed to one or more ADCs. The output of the ADC is coupled to the electronic functional block 900D. Third functional block 900C relates to the other sensors including, but not limited to, ambient temperature, pressure, humidity, diffuser temperature, internal temperature, and accelerometer. The outputs of these being also coupled to the electronic functional block 900D.

The electronic functional block 900D therefore receives multiplexed digital data relating to the multiple wavelength channels, multiplexed data relating the photodiodes around the shadow pole, and digital data from multiple environmental sensors. These are processed by a microcontroller within the electronic functional block 900D via a software algorithm or software algorithms stored in memory associated with the microcontroller. The electronic functional block 900D also implements one or more communication protocols such that the raw and/or processed data are pushed to or pulled to a host computer, in this instance a remote server 910 via a network 950. The remote server 910 processes the data from the SolarSIM-G or stores processed data from the SolarSIM-G. This data may include, but is not limited to, global spectral irradiance (horizontal or titled), direct spectrum, diffuse spectrum, spectral water vapour, aerosols, and ozone absorption profiles.

Figure 10:
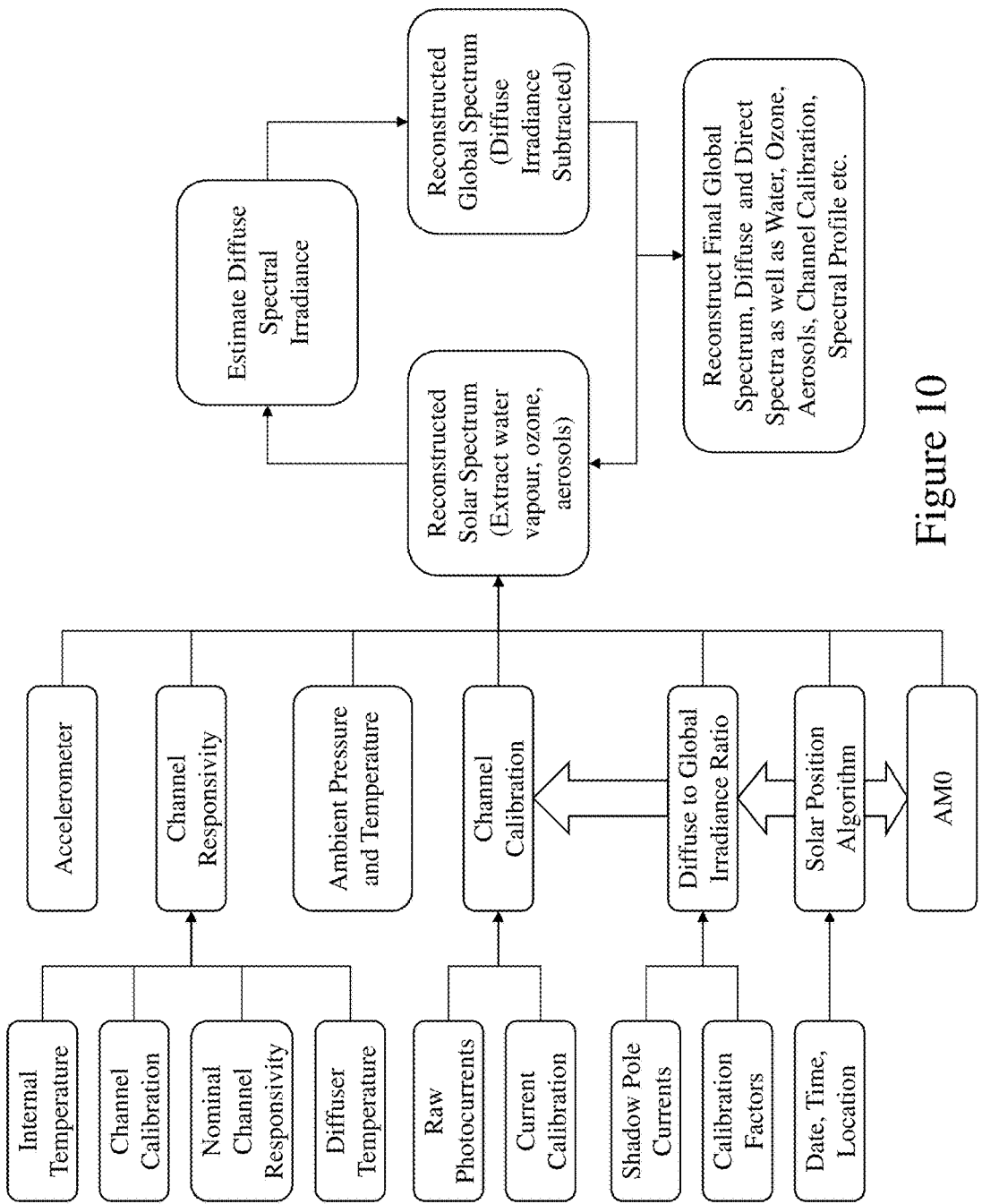
FIG. 10 depicts a processing flow for result generation for a SolarSIM-G according to an embodiment of the invention depicted in FIG. 1.

A software block diagram for the software algorithm of a SolarSIM-G is depicted in FIG. 10. As indicated all of the inputs on the left are fed to a series of initial processing algorithms and subsequent reconstruction algorithms in order to resolve the global, direct and diffuse solar spectrum. Accordingly, as indicated the channel responsivity is derived in dependence upon the internal SolarSIM-G temperature, the channel calibration, the nominal channel responsivity and the diffuser temperature. The raw digitized photocurrents and current calibration data are used, with or without the diffuse to global irradiance ratio to generate (final) calibrated channel data. This diffuse to global irradiance ratio being generated in dependence upon the shadow pole photodetector currents, their calibration data, and solar position data derived from a solar position algorithm exploiting date, time, and location data. This solar position data also defines the air mass zero (AM0) spectrum which is that of the sun with no intervening atmosphere. These outputs are combined with accelerometer, ambient pressure and ambient temperature in an initial algorithm to derive a reconstructed solar spectrum with extracted water vapour, aerosols, and ozone as a result of the wavelengths selected for the six channels.

Next the diffuse spectral irradiance is estimated and then employed to generate a refined reconstructed solar spectrum which is then employed to reconstruct the final global spectrum, diffuse and direct spectra as well as the atmospheric absorption profiles for water, ozone, and aerosols.

As the global spectrum is a combination of the direct and the diffuse spectral irradiances, the first reconstruction will not be perfect, as we are not taking the diffuse irradiance into account. However, the reconstructed proxy spectrum allows estimating the aerosols, water vapour and ozone content in the atmosphere, which in turn allow a better approximation of the diffuse irradiance (which is further enhanced by the global to diffuse ratio as determined by the shadow pole photodiodes). The approximated diffuse irradiance is then subtracted from the proxy global solar spectrum and reconstruction is performed once again, which gives the direct component of the global spectral irradiance. Addition of the estimated diffuse spectral irradiance to the direct component yields the global spectral irradiance.

The embodiment of the invention described and depicted in respect of FIG. 9 exploits six wavelength channels at CWLs of 410-430 nm, 480-505 nm, 600-620 nm, 670-690 nm, 860-880 nm, and 930-960 nm. Referring to Table 1 the association of these wavelengths to atmospheric components are listed.

TABLE 1

Bandpass Filter CWL Association to Atmospheric Components

| Channel CWL (nm) | Atmospheric Component |
|---|---|
| 410-430 | Aerosols |
| 480-505 | Aerosols |
| 600-620 | Ozone |
| 670-690 | Aerosols |
| 860-880 | Aerosols |
| 820-850, 930-960 | Water vapour |

For aerosols, other wavelengths may be considered including, for example, CWLs of 770-790 nm, 1040-1060 nm, 1240-1260 nm, and 1640-160 nm. Beneficially, wavelengths below approximately 1100 nm can be detected with silicon photodetectors whereas longer wavelengths require germanium (Ge) or indium gallium arsenide (InGaS) photodetectors.

Figure 11:
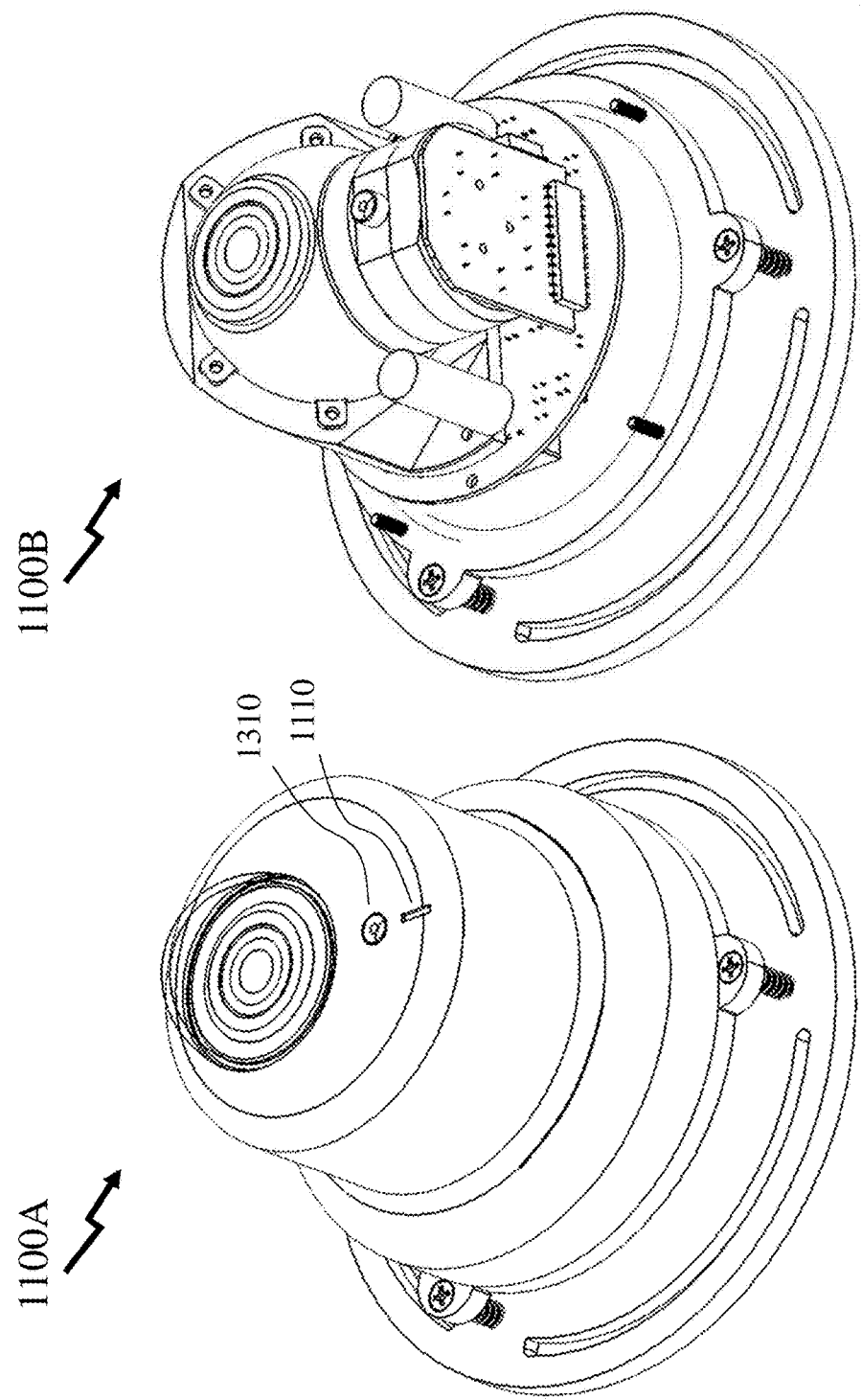
FIG. 11 depicts a global solar spectral irradiance meter (SolarSIM-G) according to an embodiment of the invention with protective dome and outer mechanical housing attached and removed.

Now referring to FIG. 11 there are depicted first and second three-dimensional (3D) perspective views 1100A and 1110B respectively of a SolarSIM-G according to an embodiment of the invention with and without a protective dome and outer mechanical housing attached. Disposed within the top surface of the SolarSIM-G depicted in first and second 3D perspective views 1100A and 1110B respectively are tilt bubble 1310 and solar noon indicator 1110. The solar noon indicator 1110 must be positioned so that it points toward the solar noon at the location of the SolarSIM-G installation, for example due south in the northern hemisphere. It would be evident from FIG. 12 that the optical train from the integrating sphere (spherical diffuser) lies along this line such that the optical collimators are aligned north-south.

Figure 12:
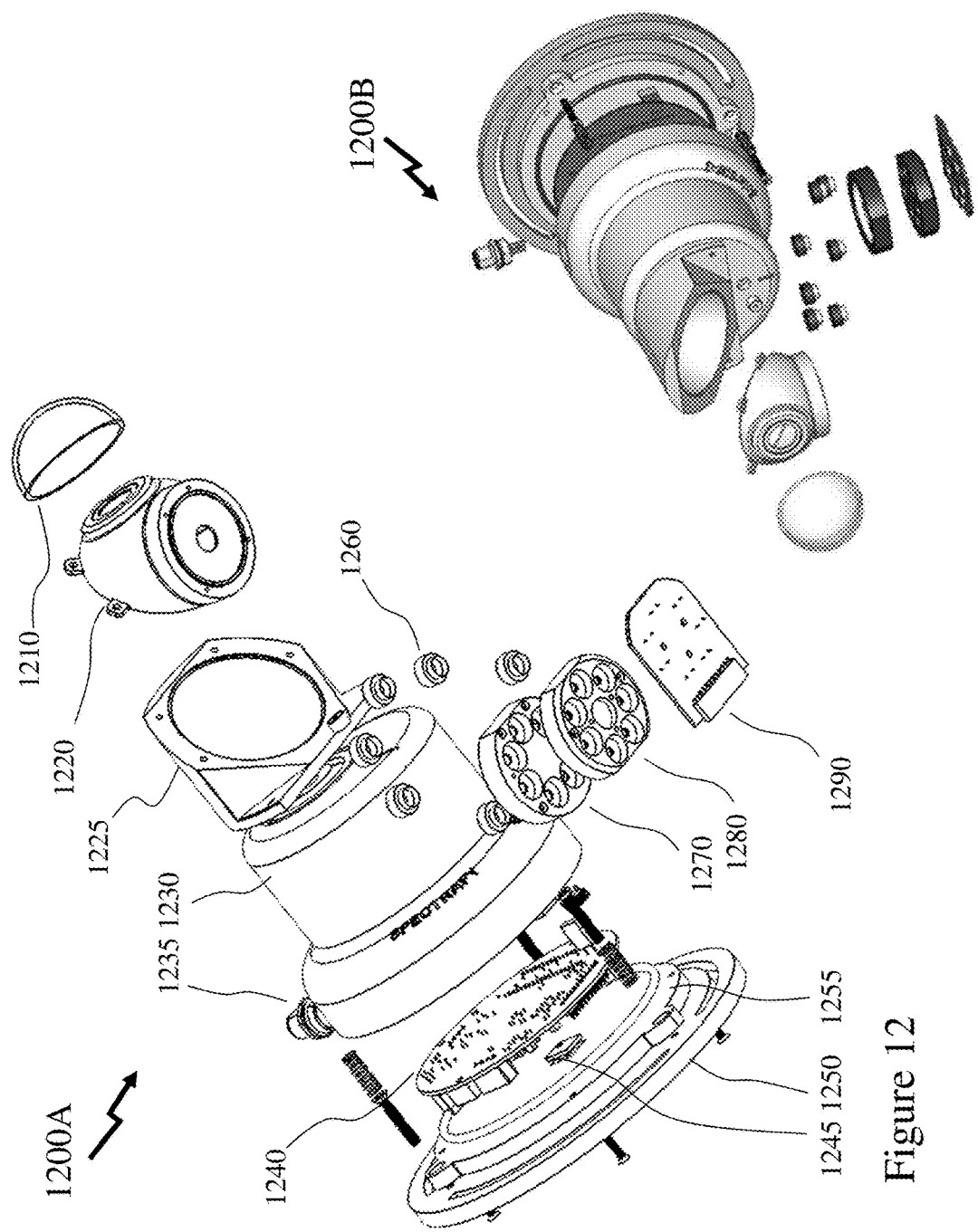
FIG. 12 depicts exploded views of the SolarSIM-G housing according to an embodiment of the invention depicted in FIG. 11.

In FIG. 12 first and second 3D perspective views 1200A and 1200B respectively are depicted of the SolarSIM-G of FIG. 11 as an exploded assembly from two different perspective viewpoints. The SolarSIM-G depicted in FIGS. 11 and 12 being a 7 channel design operating over a predetermined wavelength range, e.g. 280 nm≤λ≤4000 nm. Accordingly, the descriptions in respect of FIGS. 13 to 17 reflect this 7 channel design but it would be evident to one of skill in the art that alternate embodiments with varying channel counts may be implemented. Accordingly, as depicted within FIG. 12 and first perspective view 1200A the elements include Protective dome 1210;
Upper diffuser body 1220;
Lower diffuser body 1225;
Outer mechanical housing 1230;
Electrical connector 1235;
Electrical circuit board 1240;
Ambient environment sensor(s) 1245;
Mounting plate 1250;
SolarSIM-G base plate 1255;
Optical filter assembly 1260;
First optical collimator element 1270;
Second optical collimator element 1280; and
Photodetector circuit board 1290.

Figure 13:
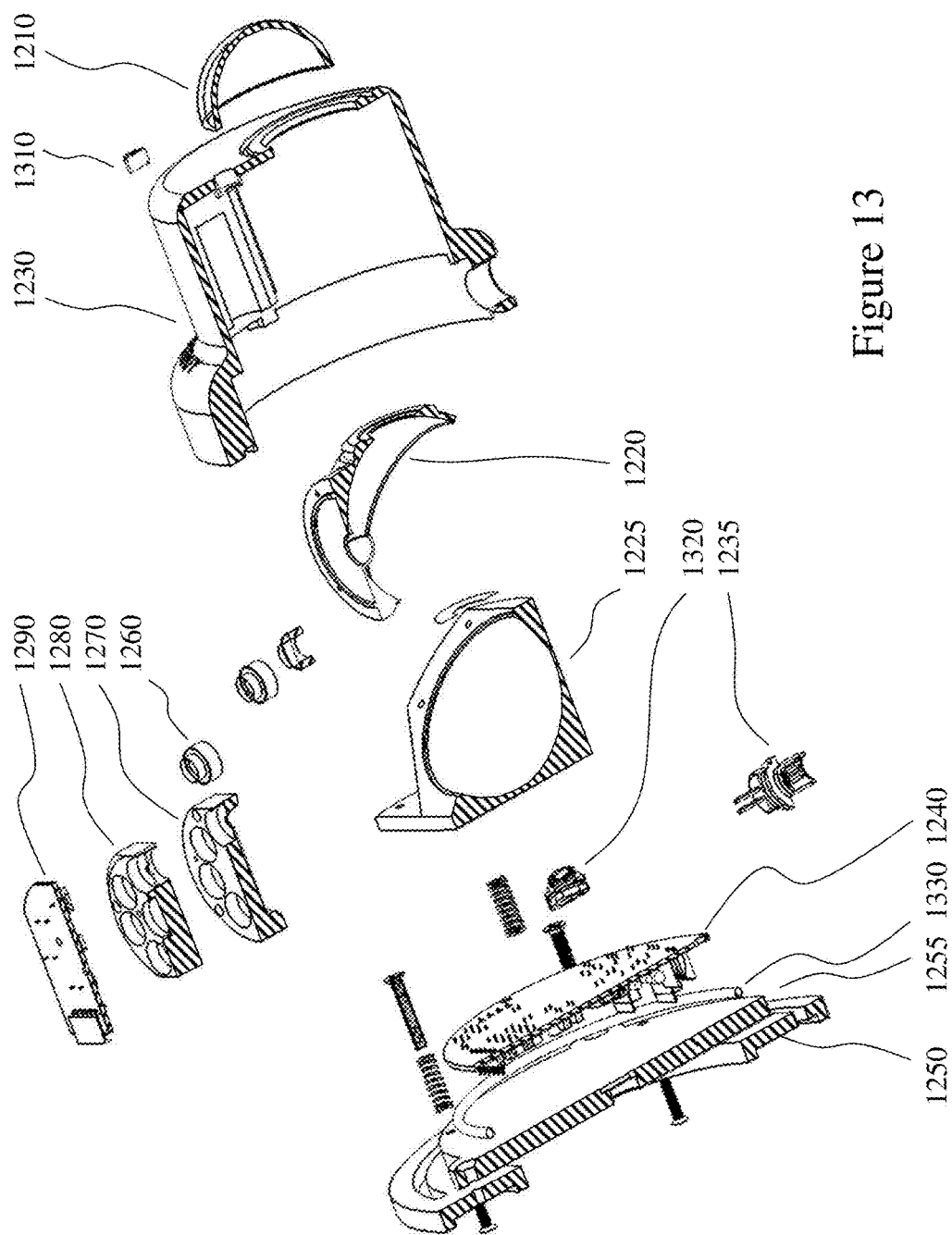
FIG. 13 depicts an exploded cross-sectional assembly view of the SolarSIM-G according to an embodiment of the invention depicted in FIGS. 11 to 12.

FIG. 13 depicts an exploded cross-sectional assembly view of the SolarSIM-G according to an embodiment of the invention depicted in FIGS. 11 and 12 where the outer mechanical housing 1230 and protective dome 1210 are depicted in correct physical relationship rather than for compact presentation in FIG. 12. Accordingly, as depicted these elements are:

Protective dome 1210;
Tilt bubble 1310;
Outer mechanical housing 1230;
Upper diffuser body 1220;
Lower diffuser body 1225;
Electrical connector 1235;
Electrical circuit board 1240;
Gore™ vent 1320;
O-ring 1330;
SolarSIM-G base plate 1255;
Mounting plate 1250;
Optical filter assembly 1260;
First optical collimator element 1270;
Second optical collimator element 1280; and
Photodetector circuit board 1290.

Figure 14:
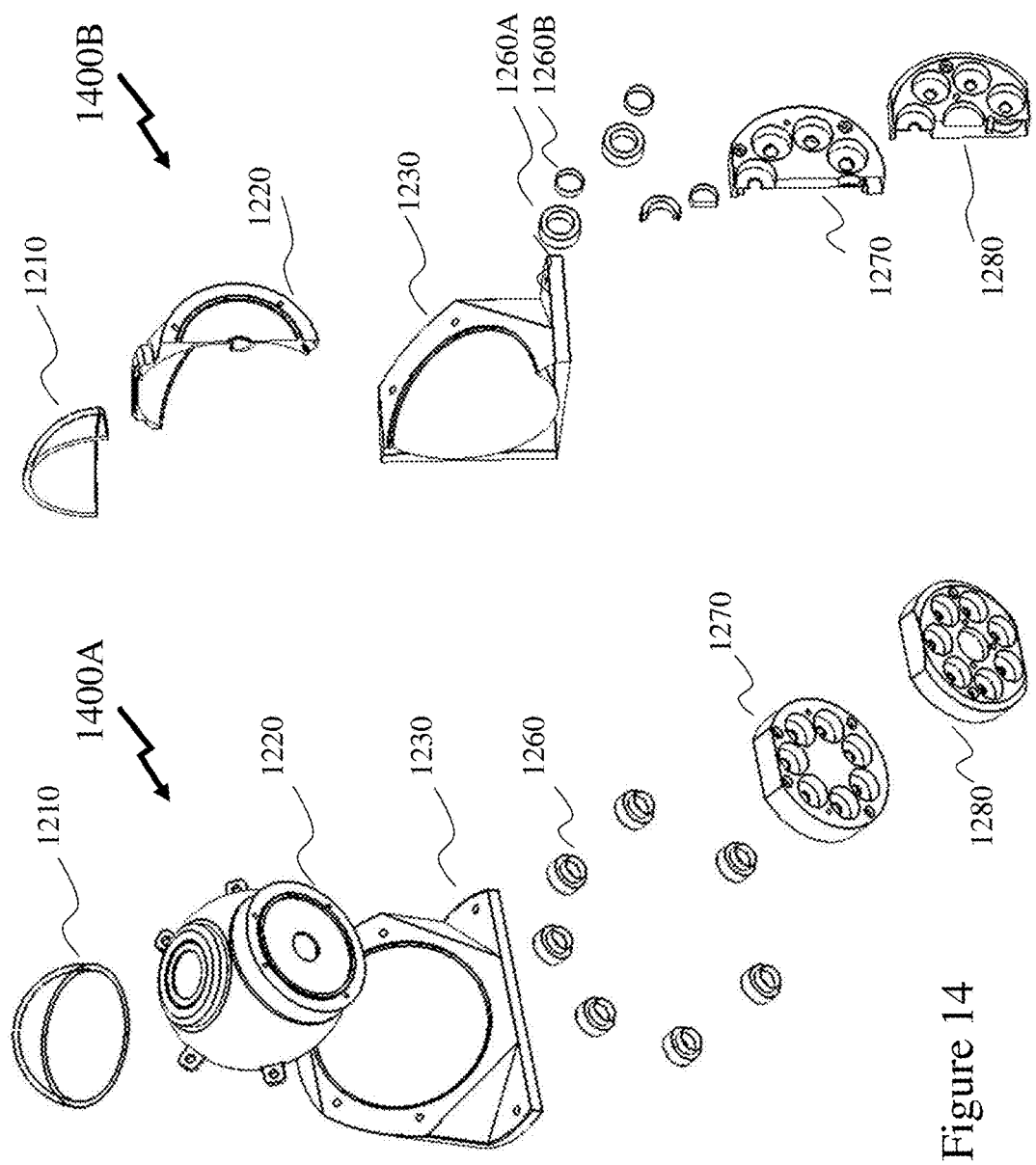
FIG. 14 depicts exploded and exploded cross-section assembly views of the optical diffuser-filter-optical collimator elements within the SolarSIM-G according to an embodiment of the invention depicted in FIGS. 11 to 13.
Figure 15A:
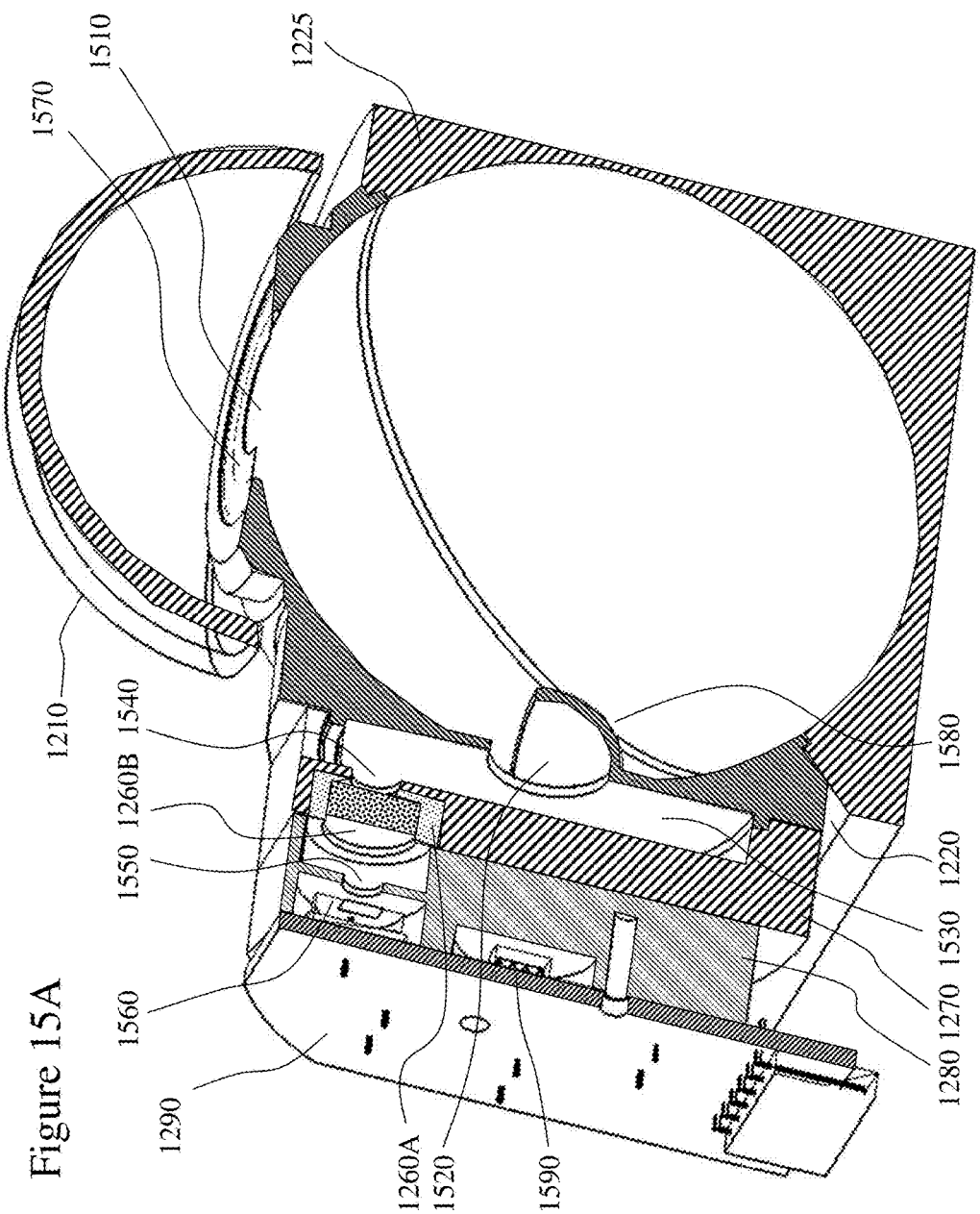
FIG. 15A depicts a cross-section assembly view of the optical sub-assembly comprising optical diffuser-filter-optical collimator-and photodetector elements within the SolarSIM-G according to an embodiment of the invention depicted in FIGS. 11 to 14.

FIG. 14 depicts exploded cross-section assembly views of the optical diffuser-filter-optical collimator elements within the SolarSIM-G according to an embodiment of the invention depicted in FIG. 11 wherein each optical filter assembly 1260 comprises an optical filter 1260B within a housing 1260A. In contrast FIG. 15A depicts a cross-section assembly view of the optical sub-assembly comprising optical diffuser-filter-optical collimator-and photodetector elements within the SolarSIM-G according to an embodiment of the invention depicted in FIGS. 11 to 14 respectively allowing the optical path from external ambient environment to each of the photodetectors 1560 on the photodetector circuit board 1290. Also depicted is the internal temperature sensor 1590.

Figure 15B:
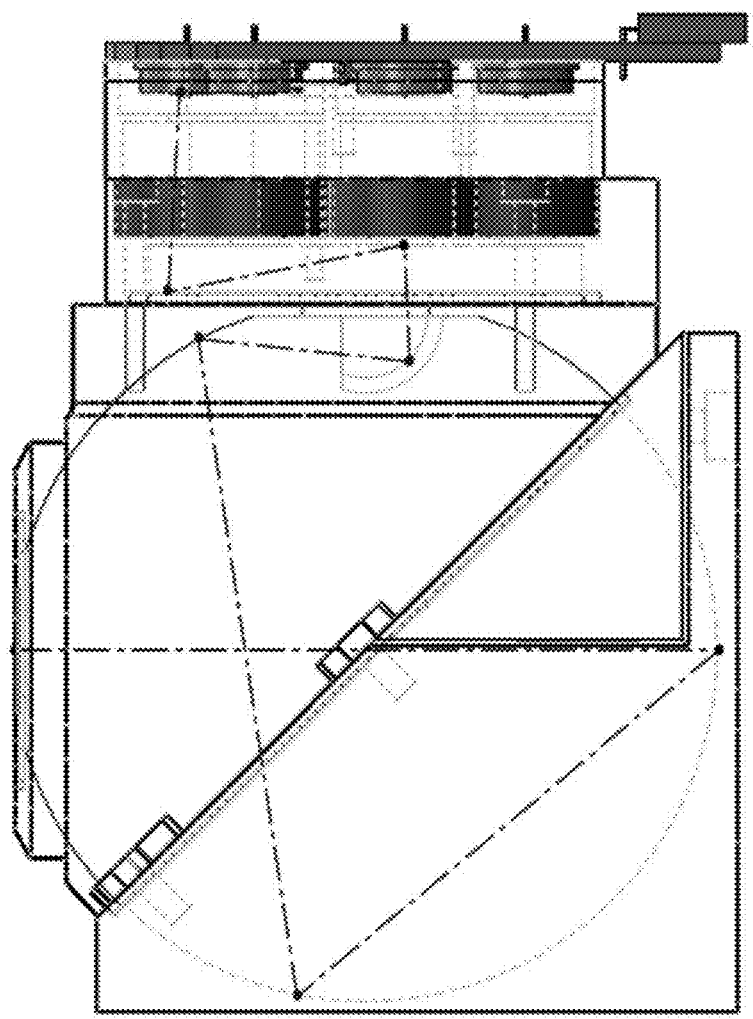
FIG. 15B depicts a single ray tracing within a SolarSIM-G according to an embodiment of the invention depicted in FIGS. 11 to 14.

Now referring to FIG. 15B a single normal incident axial ray is traced within the optical assembly. Accordingly, light from the ambient environment passes through the protective dome 1210 and a portion of this light will pass through the precision aperture 1510 formed from aperture ring 1570 fitted to the upper diffuser body 1220. Accordingly, this light therefore reflects and diffuses within the integrating sphere (spherical diffuser) formed from the mating of upper diffuser body 1220 and lower diffuser body 1225 before exiting through outlet aperture 1520 formed in the lateral wall of the upper diffuser body 1220 into diffuser cavity 1530 formed by the first optical collimator element 1270 and the outer wall of the upper diffuser body 1220.

Disposed within the region around the lower half of the outlet aperture 1520 is diffuser baffle 1580 which prevents direct reflective paths from the precision aperture 1510 to the outlet aperture. The inner surfaces of the integrating sphere (spherical diffuser) formed by the mating of upper diffuser body 1220 and lower diffuser body 1225 are within an embodiment of the invention coated with a paint providing broad spectral Lambertian-like light diffusion across the wavelength range of interest, e.g. a white paint. Within other embodiments of the invention these inner surfaces may be roughened via sand blasting, for example, rather than as machined.

The light within the diffuser cavity 1530, which may be similarly coated and treated as the inner surfaces of the integrating sphere (spherical diffuser), is then coupled via the optical collimator formed by the first and second optical collimator elements 1270 and 1280 respectively to each photodetector 1560 and their associated electronics on photodetector circuit board 1290. Disposed within each optical collimator formed by the first and second optical collimator elements 1270 and 1280 respectively is an optical filter 1260B within its housing 1260A. Within the first and second optical collimator elements 1270 and 1280 respectively are first and second collimator apertures 1540 and 1550. Accordingly, the overall combination of optical elements provides the desired cosine response in respect of the performance of the SolarSIM-G.

Figure 15C:
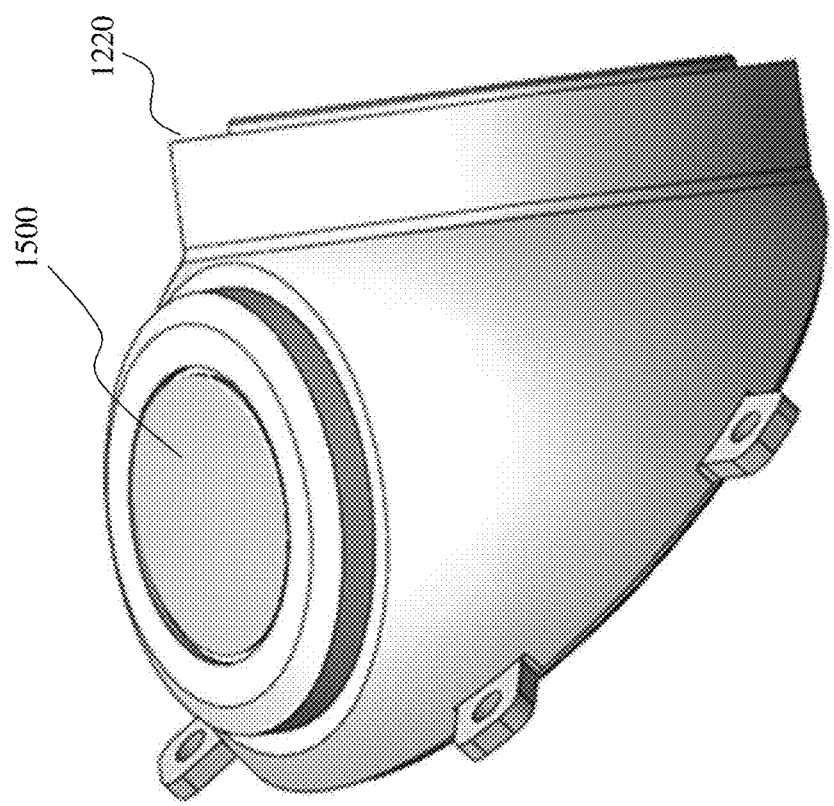
FIG. 15C depicts a SolarSIM-G according to an embodiment of the invention.

Now referring to FIG. 15C there is depicted a variant of the SolarSIM-G depicted in FIGS. 11 to 15B wherein the precision optical aperture and protective dome on the top of integrating sphere (spherical diffuser) 1220 are replaced with a diffuser element 1500, such as one formed from PTFE for example. This diffuser element 1500 may provide an improved cosine response relative to the precision aperture within the thin sheet.

Figure 16:
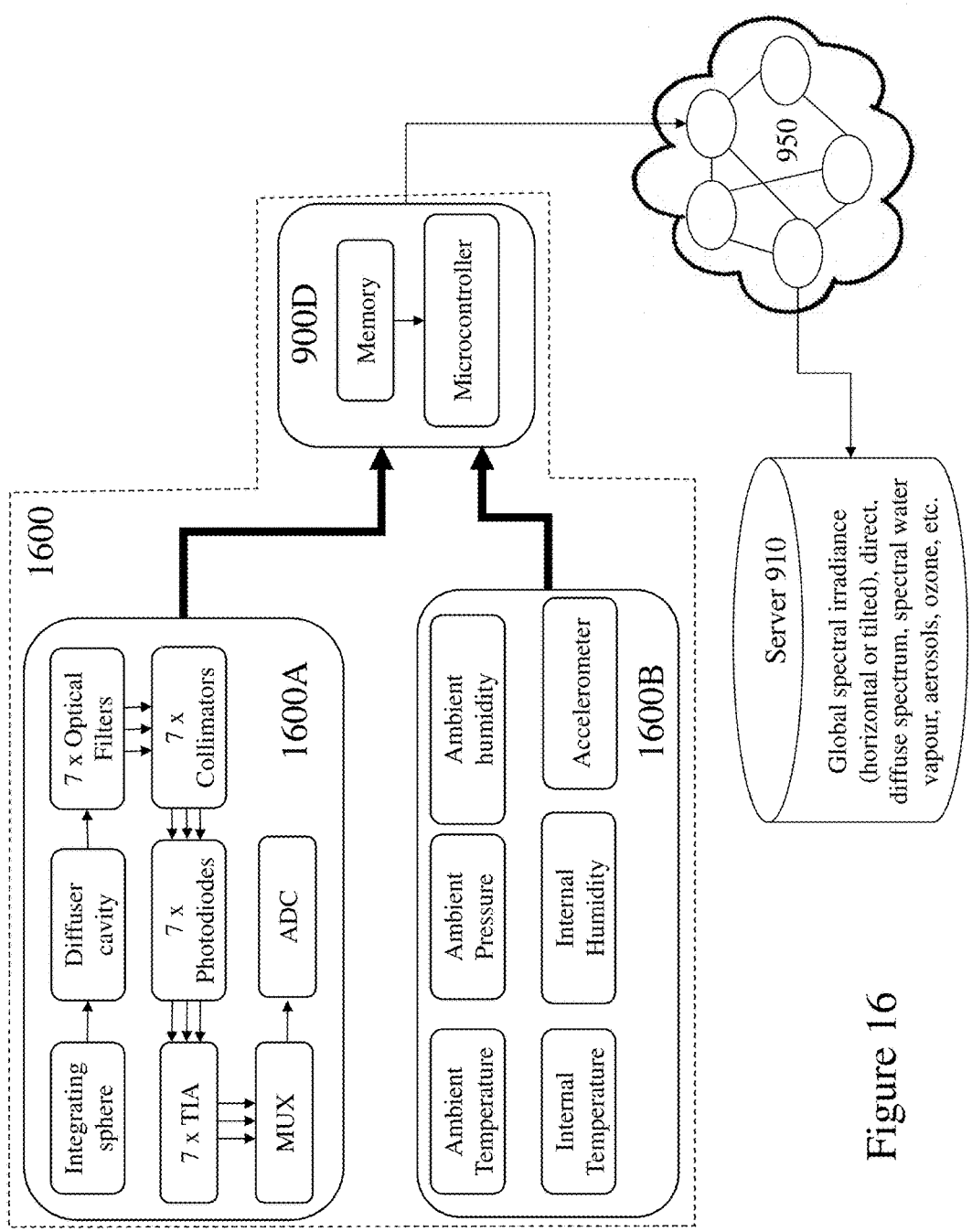
FIG. 16 depicts an assembly structure and data flow for a SolarSIM-G according to an embodiment of the invention depicted in FIG. 11.

Now referring to FIG. 16 there is depicted an exemplary system block diagram of a SolarSIM-G 1600 according to an embodiment of the invention as depicted in FIGS. 11 to 15 respectively comprising first to third functional blocks 1600A, 1600B and 900D of the SolarSIM-G 1600. As depicted first functional block 1600A relates to the multiple wavelength channels and consists of integrating sphere (spherical diffuser) and diffuser cavity 1530 which are common to all channels and then for each wavelength an optical filter and optical collimator assembly coupled to a photodiode and then the outputs from the multiple photodetectors are coupled via an array of transimpedance amplifiers (TIAs) to an electrical multiplexer. The output of the multiplexer is converted to digital form via an analog-to-digital converter (ADC). The output of the ADC is coupled to the electronic functional block 900D. Within another embodiment of the invention each photodetector has an associated TIA and the multiple TIA outputs are multiplexed for the ADC or even multiple ADCs may be employed. Optionally, the outputs from the photodetectors are multiplexed prior to being amplified by a TIA and digitized.

Second functional block 1600C relates to the other sensors within the SolarSIM-G 1600 including, but not limited to, ambient temperature, ambient pressure, ambient humidity, internal temperature, internal humidity and accelerometer. The outputs of these being also coupled to the electronic functional block 900D.

The electronic functional block 900D therefore receives multiplexed digital data relating to the multiple wavelength channels and digital data from multiple environmental sensors. These are processed by a microcontroller within the electronic functional block 900D via a software algorithm or software algorithms stored in memory associated with the microcontroller. The electronic functional block 900D also implements one or more communication protocols such that the raw and/or processed data are pushed to or pulled to a host computer, in this instance a remote server 910 via a network 950. The remote server 910 processes the data from the SolarSIM-G or stores processed data from the SolarSIM-G. This data may include, but is not limited to, global spectral irradiance (horizontal or titled), direct spectrum, diffuse spectrum, spectral water vapour, aerosols, and ozone absorption profiles. Optionally, the data acquired by the SolarSIM-G is processed directly onboard the SolarSIM-G prior to be transmitted to the remote server 910 or another device via the network 950.

The SolarSIM-G may employ one or more wireless interfaces to communicate with the network 950 selected from the group comprising, but not limited to, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-1000. Alternatively, the SolarSIM-G may employ one or more wired interfaces to communicate with the network 950 selected from the group comprising, but not limited to, DSL, Dial-Up, DOCSIS, Ethernet, G.hn, ISDN, MoCA, PON, and Power line communication (PLC).

Figure 17:
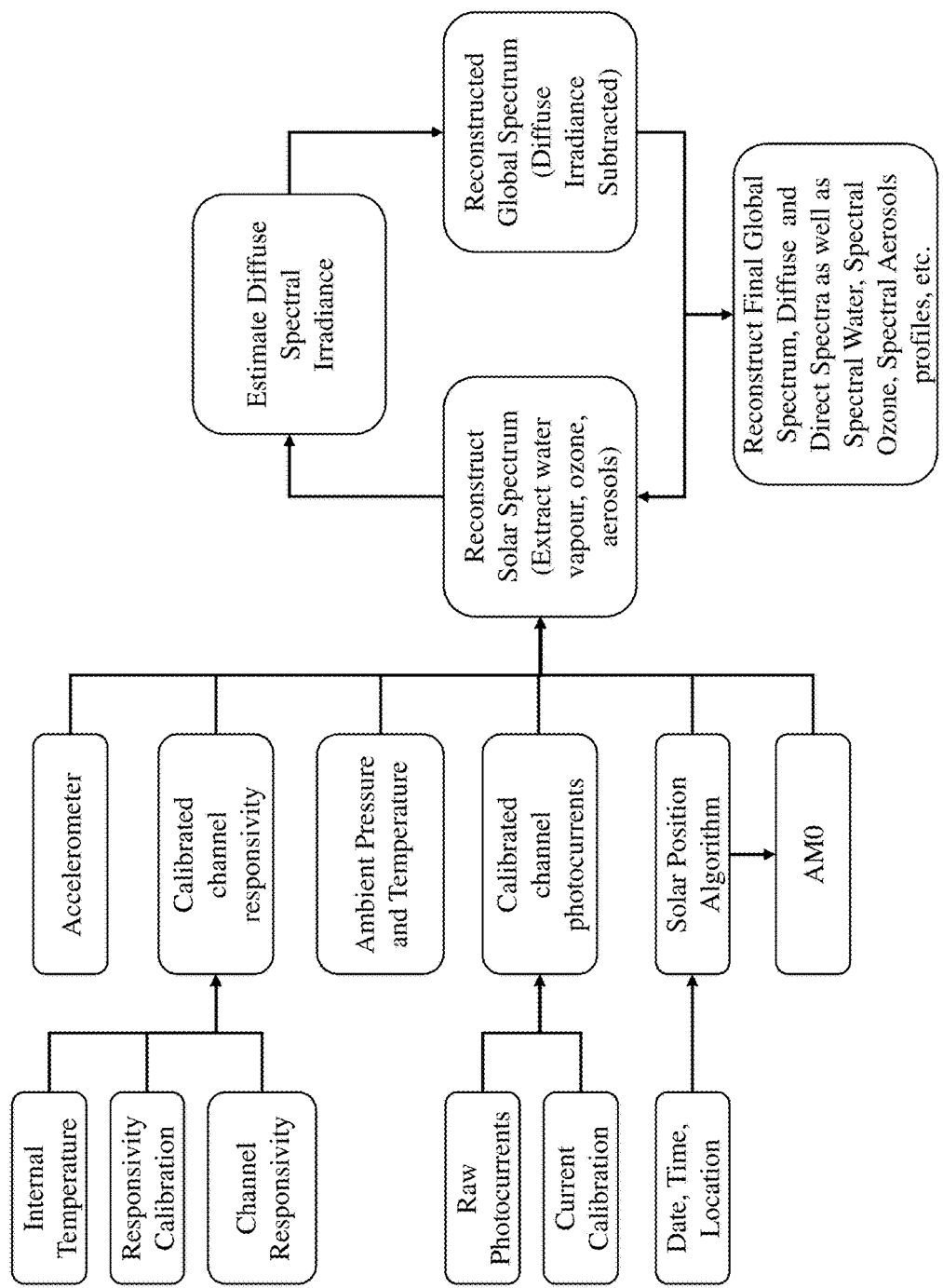
FIG. 17 depicts a processing flow for result generation for a SolarSIM-G according to an embodiment of the invention depicted in FIG. 11.

A software block diagram for the software algorithm of a SolarSIM-G is depicted in FIG. 17. As indicated all of the inputs on the left are fed to a series of initial processing algorithms and subsequent reconstruction algorithms in order to resolve the global, direct and diffuse solar spectrum. Accordingly, as indicated the channel responsivity is derived in dependence upon the internal SolarSIM-G temperature, the channel responsivity calibration and the channel responsivity. The raw digitized photocurrents and current calibration data are used to generate calibrated channel photocurrents. The date, time, and location information are employed within a solar position algorithm which is employed in generating the air mass zero (AM0) spectrum which is that of the sun with no intervening atmosphere. These outputs are combined with accelerometer, ambient pressure and ambient temperature in an initial algorithm to derive a reconstructed solar spectrum with extracted water vapour, aerosols, and ozone as a result of the wavelengths selected for the seven channels of the SolarSIM-G.

Next the diffuse spectral irradiance is estimated and then employed to generate a refined reconstructed solar spectrum which is then employed to reconstruct the final global spectrum, diffuse and direct spectra as well as the atmospheric absorption profiles for water, ozone, and aerosols. As the global spectrum is a combination of the direct and the diffuse spectral irradiances, the first reconstruction will not be perfect, as we are not taking the diffuse irradiance into account. However, the reconstructed proxy spectrum allows estimating the aerosols, water vapour and ozone content in the atmosphere, which in turn allow a better approximation of the diffuse irradiance (which is further enhanced by the global to diffuse ratio as determined by the shadow pole photodiodes). The approximated diffuse irradiance is then subtracted from the proxy global solar spectrum and reconstruction is performed once again, which gives the direct component of the global spectral irradiance. Addition of the estimated diffuse spectral irradiance to the direct component yields the global spectral irradiance.

The SolarSIM-G depicted in FIGS. 11 to 15A is mounted to a surface via the mounting plate 1250 which permits rotation of the SolarSIM-G prior to locking it down. The SolarSIM-G itself is mounted via its baseplate 1255 to the mounting plate 1250 by 3 screws with springs allowing the SolarSIM-G to be levelled via adjustment of these screws and the tilt bubble 1310. The outer mechanical housing 1230 is attached to the baseplate 1255 via a series of screws and disposed within the baseplate 1255 is a vent 1320 which allows pressure equalization for the outdoor environment sensor to measure ambient pressure, temperature and humidity. Vent 1320 provides for pressure equalization of the internal environment of the SolarSIM-G with the ambient environment whilst acting as a barrier to liquids such as water and particulates such as dust.

On the upper side of the SolarSIM-G depicted in FIGS. 11 to 15A the protective dome 1210 fits within a groove formed in the upper surface of the outer mechanical housing 1230 and is adhered in position by a material such as a silicone or an epoxy for example. The precision aperture 1510 is formed by the inner opening within the aperture ring 1570 which is formed from a very thin piece of material, e.g. 80 µm high purity nickel sheet, as this ideally should be zero thickness and perfectly reflective, the former to avoid cosine losses and the latter to aid light diffusion within the integrating sphere (spherical diffuser). This aperture ring 1570 is similarly sealed against the precision aperture 1510 via silicone although a mechanical attachment may also be employed.

The upper and lower diffuser bodies 1220 and 1225 form an integrating sphere (spherical diffuser) that creates, ideally, a perfect cosine response and the inner surfaces are coated with a highly Lambertian material to provide a Lambertian reflectance which is an "ideal" matte or diffusively reflecting surface with apparent brightness constant with observation angle. Within the embodiment depicted the upper and lower diffuser bodies 1220 and 1225 are joined via screws with a lipped joint between although within other embodiments of the invention an O-ring or other seal may be employed as may other means of joining the upper and lower diffuser bodies 1220 and 1225 together. The diffuser is then mounted to the baseplate 1255 via screws.

Within the upper diffuser body 1220 is the output aperture 1520 which has formed around its lower half the diffuser baffle 1580 which is used to prevent a first reflection from the integrating sphere (spherical diffuser) at near normal incidence illumination. The diffuser baffle 1580 is spherical to allow for azimuthal symmetry, which improves the cosine response. The output aperture 1520 allows light to enter the diffusing cavity 1530 which allows the rays to undergo multiple reflections for optimal diffusion. This diffusing cavity 1530 being formed from the upper diffuser body 1220 and first optical collimator element 1270.

Within the first optical collimator element 1270 are first collimator apertures 1540 for each wavelength channel. Mounted to the first optical collimator element 1270 is second optical collimator element 1280 which has wells machined within to house the optical filters 1260B and their housings 1260A. Also formed within second optical collimator element 1280 are second collimator apertures 1550 which in conjunction with the first collimator apertures 1540 define the angular distribution of light rays allowed to strike each detector. This being necessary as the performance of bandpass filters degrades as the incidence angle increases and accordingly only near collimated light, in reality an approximately 10-degree half angle, is allowed to pass to the photodetectors 1560.

Within embodiments of the invention the diffuser may be formed from one or more thermoplastics, polyesters, and glasses according to the wavelength range, cost, diffuser performance etc. required from the diffuser. For example, the diffuser may be BK7 glass. Optionally, the enclosure, baseplate and tube collimator may be formed from a plastic, thermoplastic, polyester, or a metal or formed from different plastics, thermoplastics, polyesters, or metals. Optionally, in embodiments of the invention the mechanical structure may be encased partially or fully within a casing such as a silicone for example. Optionally, the enclosure and tube collimators may be formed as a single piece-part or two or more piece-parts.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory content. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alpha-numeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device comprising:
   a spherical diffuser comprising a spherical cavity within an outer body, the spherical cavity coated with a first near Lambertian material;
   a first aperture of a first predetermined diameter formed in a first predetermined position on the spherical diffuser;
   a second aperture of a second predetermined diameter formed in a second predetermined position on the spherical diffuser;
   a baffle disposed in a predetermined relationship relative to the first aperture and the second aperture, the baffle having a predetermined thickness, is coated with a second near Lambertian material and is disposed on the inner surface of the spherical diffuser and having a geometry defining a predetermined portion of a sphere;

a plurality of optical collimators coupled to the second aperture and defining a maximum angular acceptance angle for each photodetector of a plurality of photodetectors disposed at the distal end of an optical collimator from that coupled to the second aperture; and a plurality of optical filters, each filter having a passband of predetermined optical wavelengths and disposed in combination with an optical collimator of the plurality of collimators to filter optical signals exiting the second aperture.

2. The device according to claim 1, wherein
the spherical diffuser is attached when deployed to a baseplate mounted to a structure and the spherical diffuser is orientated such that the optical collimators are aligned north-south and point towards the solar noon at the location of the installation.

3. The device according to claim 1, further comprising
a first electronic circuit for digitizing a photocurrent generated by each photodetector of the plurality of photodetectors; and
a second electronic circuit for generating a reconstructed solar spectrum in dependence upon at least the digitized photocurrents of the plurality of photodetectors and model of the solar spectrum with no atmosphere.

4. The device according to claim 3, wherein
the reconstructed solar spectrum is at least one of a final global spectrum, a diffuse solar spectrum, and a direct solar spectrum.

5. The device according to claim 1, further comprising
generating an absorption profile relating to one of atmospheric precipitable water vapour, atmospheric ozone, and atmospheric aerosols; wherein
at least one filter of the plurality of filters has its passband of predetermined optical wavelengths established in dependence upon the one of precipitable water vapour, ozone, and atmospheric aerosols.

6. The device according to claim 1, wherein
each collimator comprises a first portion with a first diameter and a second portion with a second diameter and the associated filter of the plurality of filters is disposed between the first portion and the second portion.

7. The device according to claim 1, wherein
the first aperture of a first predetermined diameter is defined by an element formed within a sheet of predetermined thickness having high reflectivity attached to an opening within the spherical diffuser.

8. The device according to claim 7, wherein
the sheet is nickel and the predetermined thickness is less than 100 µm.

9. The device according to claim 1, wherein
at least one of:
the spherical diffuser is formed from at least two portions joined together; and
the first aperture, second aperture and baffle are all within a common portion of a plurality of portions assembled to form the spherical diffuser.

10. The device according to claim 1, further comprising
a second diffuser disposed between the second aperture and the plurality of optical collimators.

11. A device comprising:
a plurality of first photodetectors, each first photodetector receiving a predetermined wavelength range of the ambient optical environment via an optical path comprising a diffuser element, a bandpass filter, and an optical collimator to limit the angle of incident ambient light to within a predetermined range;

a plurality of second photodetectors arranged radially around a post projecting above the upper surface of the plurality of second photodetectors; and an electronic circuit comprising a first portion for digitizing a photocurrent for each first photodetector of the plurality of first photodetectors, a second portion for digitizing a photocurrent for each second photodetector of the plurality of second photodetectors, and a third portion for at least one of generating a reconstructed solar spectrum in dependence upon at least the digitized photocurrents of the plurality of first photodetectors, the digitized photocurrents of the plurality of second photodetectors, and a model of the solar spectrum with no atmosphere.

12. The device according to claim 11, wherein
the reconstructed solar spectrum is at least one of a final global spectrum, a diffuse solar spectrum, and a direct solar spectrum.

13. The device according to claim 11, further comprising
generating an atmospheric absorption profile relating to at least one of precipitable water vapour, ozone, an atmospheric aerosol and atmospheric aerosols.

14. The device according to claim 11, wherein
in deployment the plurality of first detectors are disposed towards the north and the plurality of second detectors are disposed to the south.

15. The device according to claim 11, wherein
the diffuser element associated with each first photodetector of the plurality of first photodetectors is designed in dependence upon the predetermined wavelength associated with the corresponding bandpass filter and the material from which the diffuser element is formed.

16. The device according to claim 11, further comprising
an environmental sensing circuit comprising at least one of a humidity sensor, a pressure sensor and a temperature sensor disposed within the device and coupled to the external environment of the device by a vent, the vent allowing passage of air but not water.

17. The device according to claim 11, wherein
the plurality of second photodetectors consist of one or more photodiode arrays.

18. A device comprising:
a plurality of wavelength filtered photodetectors each receiving light from the ambient environment within a predetermined wavelength range and within a predetermined angle of incidence to the normal of the photodetector;
a plurality of second photodetectors each receiving light from the ambient environment;
a shadow pole disposed with respect to the plurality of second photodetectors; and
an optical element disposed on a front face of the device comprising:
a first uniform transparent region disposed in front of the plurality of second photodetectors and a second diffuser region comprising a plurality of features, each feature designed in dependence upon a predetermined wavelength associated with a wavelength filtered photodetector and the material from which the optical element is formed;
a transparent dome that sits above the front surface of the device and protects the diffuser, shadow pole and second plurality of photodiodes from the elements.

19. The device according to claim 18, wherein in deployment the plurality of first detectors are disposed towards the north and the plurality of second detectors are disposed to the south.

20. The device according to claim 18, further comprising an environmental sensing circuit comprising at least a humidity sensor disposed within the device and coupled to the internal environment of the device by a vent, the vent allowing passage of air but not water.

21. The device according to claim 18, wherein the plurality of second photodetectors are disposed radially around the shadow pole such that an estimate of the ratio of received diffuse light to received direct light can be obtained from the plurality of photocurrents from the plurality of second photodetectors.

22. The device according to claim 18, wherein the reconstructed solar spectrum is at least one of a final global spectrum, a diffuse solar spectrum, and a direct solar spectrum.

23. The device according to claim 18, further comprising generating an atmospheric absorption profile relating to at least one of precipitable water vapour, ozone, an atmospheric aerosol and atmospheric aerosols.

24. The device according to claim 18, wherein the plurality of second photodetectors are a photodiode array.

25. The device according to claim 18, further comprising a protective element disposed to protect the diffuser from the ambient environment and allow sunlight to impinge directly on the shadow pole and the plurality of second photodetectors.

26. The device according to claim 25, further comprising a fan disposed to blow air across the protective element.

* * * * *